(12) United States Patent
Gerber et al.

(10) Patent No.: US 8,958,870 B2
(45) Date of Patent: Feb. 17, 2015

(54) THERAPY PROGRAM MODIFICATION

(75) Inventors: Martin T. Gerber, Maple Grove, MN (US); John C. Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 302 days.

(21) Appl. No.: 12/989,740

(22) PCT Filed: Jan. 23, 2009

(86) PCT No.: PCT/US2009/031806
§ 371 (c)(1),
(2), (4) Date: Oct. 26, 2010

(87) PCT Pub. No.: WO2009/134478
PCT Pub. Date: Nov. 5, 2009

(65) Prior Publication Data
US 2011/0040546 A1   Feb. 17, 2011

Related U.S. Application Data

(60) Provisional application No. 61/048,762, filed on Apr. 29, 2008.

(51) Int. Cl.
*A61N 1/37* (2006.01)
*A61N 1/372* (2006.01)
*A61N 1/36* (2006.01)

(52) U.S. Cl.
CPC .............. *A61N 1/37* (2013.01); *A61N 1/37247* (2013.01); *A61N 1/36071* (2013.01)
USPC .................... 607/2; 607/9; 600/114; 600/115

(58) Field of Classification Search
CPC ........... A61N 1/36128; A61N 1/36146; A61N 1/36185; A61N 1/37235; A61N 1/37247; A61N 1/37264

USPC ....................... 600/114, 115; 607/2, 9, 30, 59
See application file for complete search history.

(56) References Cited

U.S. PATENT DOCUMENTS 5,331,966 A * 7/1994 Bennett et al. ................ 600/508
5,417,717 A * 5/1995 Salo et al. ....................... 607/18
(Continued)

FOREIGN PATENT DOCUMENTS

WO         2007097873 A1    8/2007

OTHER PUBLICATIONS

Examination Report from counterpart European Application No. 09 739 281.5, dated Mar. 13, 2014, 7 pp.
(Continued)

*Primary Examiner* — Niketa Patel
*Assistant Examiner* — Christopher A Flory
(74) *Attorney, Agent, or Firm* — Shumaker & Sieffert, P.A.

(57) ABSTRACT

A therapy program may be modified based on information indicative of a change in a therapy field, which may represent a region of a patient's tissue to which therapy is delivered. Upon receiving information indicative of a therapy field change, an algorithmic model of a present therapy field may be generated and compared to an algorithmic model of a baseline therapy field, which indicates a therapy field that provides efficacious therapy to the patient. If a characteristic of the present therapy field differs from the baseline therapy field model, the current therapy program may be modified. In another example, upon receiving information indicative of a therapy field change, the current therapy program may be modified, and an algorithmic model of a therapy field based on the modified therapy program may be compared to a baseline therapy field model to determine whether the modified therapy program is a suitable alternative.

27 Claims, 19 Drawing Sheets

(56) References Cited

U.S. PATENT DOCUMENTS

| | | | |
|---|---|---|---|
| 5,683,429 A * | 11/1997 | Mehra | 607/14 |
| 5,895,416 A * | 4/1999 | Barreras et al. | 607/62 |
| 6,980,958 B1 * | 12/2005 | Surwit et al. | 705/2 |
| 6,985,774 B2 * | 1/2006 | Kieval et al. | 607/44 |
| 7,010,347 B2 * | 3/2006 | Schecter | 607/17 |
| 7,881,805 B2 * | 2/2011 | Bradley et al. | 607/117 |
| 7,890,159 B2 * | 2/2011 | Zhang et al. | 600/512 |
| 2005/0060009 A1 * | 3/2005 | Goetz | 607/48 |
| 2007/0021797 A1 * | 1/2007 | Kieval et al. | 607/44 |
| 2007/0203541 A1 * | 8/2007 | Goetz et al. | 607/59 |
| 2007/0203546 A1 * | 8/2007 | Stone et al. | 607/59 |
| 2008/0215118 A1 * | 9/2008 | Goetz et al. | 607/59 |
| 2009/0030478 A1 * | 1/2009 | Kieval et al. | 607/44 |
| 2011/0046498 A1 * | 2/2011 | Klap et al. | 600/534 |

OTHER PUBLICATIONS

Response to European Examination Report dated Mar. 13, 2014, from counterpart European Patent Application No. 09739281.5, filed Jul. 15, 2014, 8 pp.

* cited by examiner

| FAULTY ELECTRODE | MODIFIED THERAPY PROGRAM |
|---|---|
| ELECTRODE 35A | THERAPY PROGRAM A |
| ELECTRODE 35B | THERAPY PROGRAM B |
| ELECTRODE 35C | THERAPY PROGRAM C |
| ELECTRODE 35D | THERAPY PROGRAM D |
| ELECTRODE 37A | THERAPY PROGRAM E |
| ELECTRODE 37B | THERAPY PROGRAM F |
| ELECTRODE 37C | THERAPY PROGRAM G |
| ELECTRODE 37D | THERAPY PROGRAM H |

THERAPY PROGRAM MODIFICATION

TECHNICAL FIELD

The disclosure relates to medical devices, and, more particularly, systems and methods for modifying therapy programs for therapy delivered by medical devices.

BACKGROUND

Implantable medical devices, such as electrical stimulators or therapeutic agent delivery devices, may be used in different therapeutic applications, such as deep brain stimulation (DBS), spinal cord stimulation (SCS), pelvic stimulation, gastric stimulation, peripheral nerve stimulation or delivery of pharmaceutical agent, insulin, pain relieving agent or anti-inflammatory agent to a target tissue site within a patient. A medical device may be used to deliver therapy to a patient to treat a variety of symptoms or patient conditions such as chronic pain, tremor, Parkinson's disease, other types of movement disorders, seizure disorders (e.g., epilepsy), urinary or fecal incontinence, sexual dysfunction, obesity, mood disorders, gastroparesis or diabetes. In some cases, the electrical stimulation may be used for muscle stimulation, e.g., functional electrical stimulation (FES) to promote muscle movement or prevent atrophy. In some therapy systems, an implantable electrical stimulator delivers electrical therapy to a target tissue site within a patient with the aid of one or more medical leads that include electrodes. In addition to or instead of electrical stimulation therapy, a medical device may deliver a therapeutic agent to a target tissue site within a patient with the aid of one or more fluid delivery elements, such as a catheter.

During a programming session, which may occur during implant of the medical device, during a trial session, or during a follow-up session after the medical device is implanted in the patient, a clinician may select therapy parameter values for the medical device that provide efficacious therapy to the patient. In the case of electrical stimulation, the therapy parameters may include an electrode combination, and an amplitude, which may be a current or voltage amplitude, a pulse width, and a pulse rate for stimulation signals to be delivered to the patient. In the case of a therapeutic agent delivery device, the therapy parameters may include a dose (e.g., a bolus or a group of boluses) size, a frequency of bolus delivery, a concentration of a therapeutic agent in the bolus, a type of therapeutic agent to be delivered to the patient (if the medical device is configured to deliver more than one type of agent), a lock-out interval, and so forth.

A group of therapy parameter values may be referred to as a therapy program. A medical device may deliver therapy to a patient according to one or more stored therapy programs.

SUMMARY

In general, the disclosure is directed to modifying a therapy program based on information indicative of a change in a therapy field. A therapy field represents a region of the patient's tissue to which therapy is delivered. In some examples, the therapy field is based on an electrical field that is generated based upon a patient's anatomy and a therapy program defining stimulation parameter values, where the electrical field represents the regions of the patient's anatomical region that will be covered by an electrical field during therapy. In other examples, the therapy field is an activation field, which indicates the nerve or muscle tissue, e.g., neurons, that will be activated by the electrical field in the target anatomical region of the patient.

In some cases, a change in a therapy field may adversely affect the efficacy of therapy delivered to the patient. For example, if at least one field characteristic of a present therapy field differs from a respective field characteristic of a therapy field known to result in efficacious therapy to the patient (e.g., a "baseline" therapy field), the present therapy field may provide less than a desirable level of therapeutic efficacy. The field characteristic may include, for example, a centroid of stimulation, a volume or area (e.g., a cross-sectional slice of the volume) of stimulation, recruited neurons, an amplitude of the voltage or current at a certain spatial point within stimulation volume, a charge density, or the like.

A therapy program may be modified in response to receiving information indicative of a change in a therapy field in an attempt to maintain efficacious therapy for the patient. In the case of electrical stimulation therapy systems, the information indicative of a change in a therapy field may be, for example, a change in the impedance of one or more electrical paths including the electrodes used to deliver electrical stimulation therapy, an open circuit condition of at least one of the electrodes, a change in location or orientation of at least one of the electrodes, the distance between implanted electrodes within the patient, a change in the power available to the implanted medical device, or the like. In some examples, the information indicative of a change in a therapy field may include information indicating a change in the therapeutic efficacy of the therapy program, such as information provided by sensors that monitor a patient parameter related to the patient condition. The change in therapeutic efficacy may be reflected as an increase in patient symptoms associated with the patient condition for which the therapy system is implemented or an increase in side effects from the therapy delivery, as examples.

In some examples described herein, a therapy program is modified based on a comparison between an algorithmic model of a baseline therapy field and therapy field model generated based on a therapy program and the information indicative of the change in the therapy field. The therapy program may be modified to maintain one or more characteristics of the baseline therapy field. The algorithmic model of the baseline therapy field may be generated by computer modeling. For example, the baseline therapy field model may be an algorithmic model that is generated based on a patient anatomy, the patient's tissue characteristics, and stimulation parameter values. The baseline therapy field model may be, for example, a representation of an electrical field, current density, voltage gradient or neuron activation field.

In other examples, a therapy program is modified based on the information indicative of the change in the therapy field. For example, in the case of electrical stimulation therapy, a current or voltage amplitude of stimulation may be increased in order to compensate for a change in impedance of an electrode. In order to determine whether the modified therapy program is suitable, an algorithmic model of a therapy field resulting from the modified therapy program may be compared to an algorithmic model of a baseline therapy field.

In one aspect, the disclosure is directed to a method comprising receiving information indicative of a change in a first therapy field, wherein therapy is delivered to a patient according to a therapy program to generate the first therapy field, generating a first therapy field model based on the therapy program and the information indicative of the change in the first therapy field, comparing the first therapy field model to an algorithmic model of a baseline therapy field, and modifying the therapy program based on the comparison of the first therapy field model to the algorithmic model of the baseline therapy field.

In another aspect, the disclosure is directed to a system comprising an implantable medical device that delivers therapy to a target tissue site within a patient according to a therapy program to generate a first therapy field, a memory that stores an algorithmic model of a baseline therapy field, and a processor that receives information indicative of a change in the first therapy field, generates a first therapy field model based on the therapy program and the information indicative of the change in the first therapy field, compares the first therapy field model to the algorithmic model of the baseline therapy field, and modifies the therapy program based on the comparison of the first therapy field model to the algorithmic model of the baseline therapy field.

In another aspect, the disclosure is directed to a system comprising means for receiving information indicative of a change in a first therapy field, where therapy is delivered to a patient according to a therapy program to generate the first therapy field, means for generating a first therapy field model based on the therapy program and the information indicative of the change in the first therapy field, means for comparing the first therapy field model to an algorithmic model of a baseline therapy field, and means for modifying the therapy program based on the comparison of the first therapy field model to the algorithmic model of the baseline therapy field.

In another aspect, the disclosure is directed to a method comprising receiving information indicative of a change in a first therapy field, wherein therapy is delivered to a patient according to a therapy program to generate the first therapy field, modifying the therapy program based on the information indicative of a change in a first therapy field, generating a first algorithmic model of a modified therapy field based on the modified therapy program, and comparing at least one field characteristic of the first algorithmic model to a second algorithmic model of a baseline therapy field.

In another aspect, the disclosure is directed to a system comprising an implantable medical device that delivers therapy to a target tissue site within a patient according to a therapy program to generate a first therapy field, a memory that stores an algorithmic model of a baseline therapy field, and a processor that receives information indicative of a change in the first therapy field, modifies the therapy program based on the information indicative of a change in a first therapy field, generates a first algorithmic model of a modified therapy field based on the modified therapy program, and compares at least one field characteristic of the first algorithmic model to a second algorithmic model of a baseline therapy field.

In another aspect, the disclosure is directed to a system comprising means for receiving information indicative of a change in a first therapy field, where therapy is delivered to a patient according to a therapy program to generate the first therapy field, means for modifying the therapy program based on the information indicative of a change in a first therapy field, means for generating a first algorithmic model of a modified therapy field based on the modified therapy program, and means for comparing at least one field characteristic of the first algorithmic model to a second algorithmic model of a baseline therapy field.

DETAILED DESCRIPTION

Figure 1A:
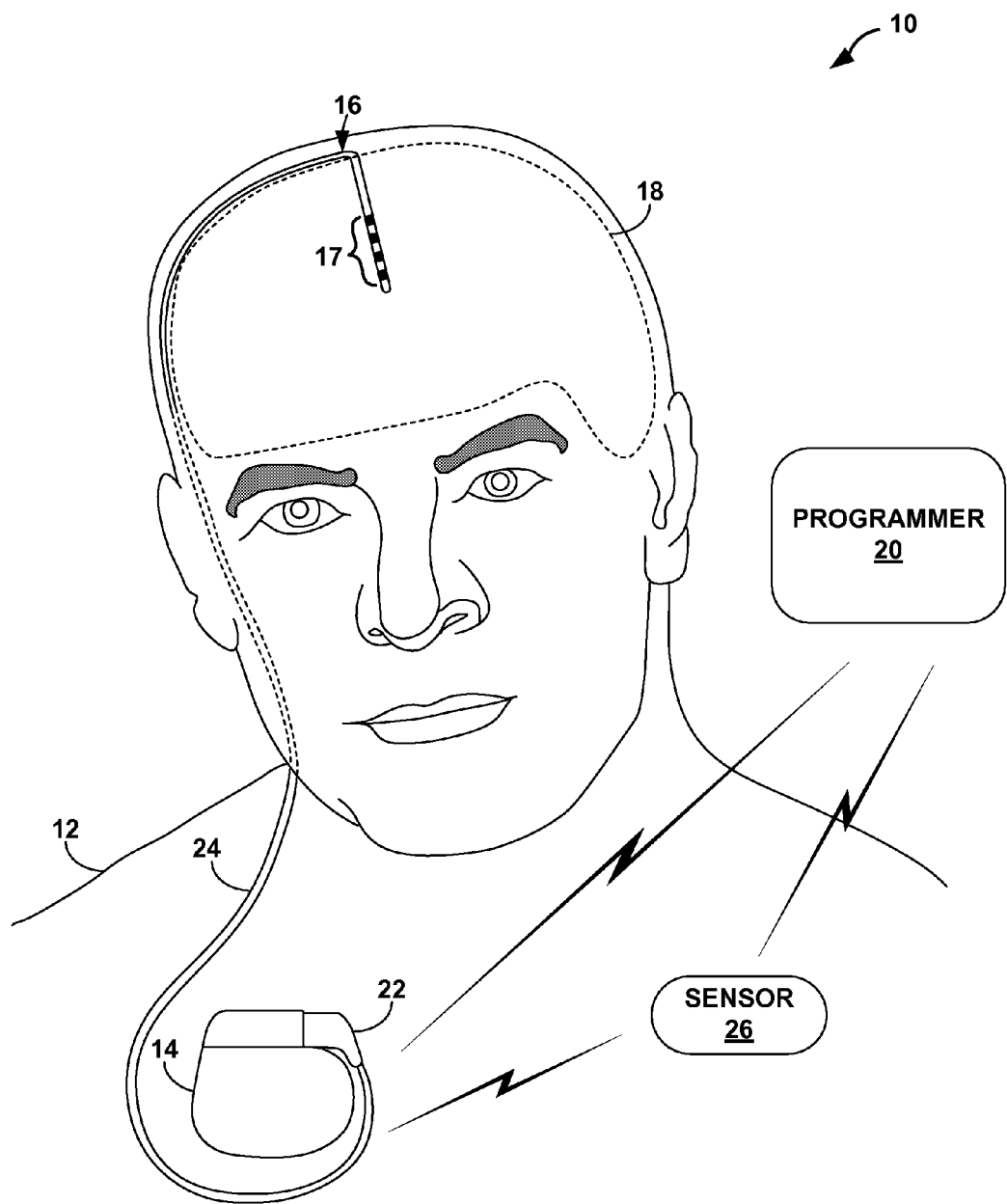
FIGS. 1A and 1B are conceptual diagrams illustrating example therapy systems that provide electrical stimulation therapy to a patient.

FIG. 1A is a conceptual diagram illustrating an example therapy system 10 that provides electrical stimulation therapy to patient 12. Therapy system 10 includes IMD 14 and medical lead 16. In the example shown in FIG. 1A, IMD 14 delivers deep brain stimulation (DBS) to tissue within brain 18 of patient 12 in order to alleviate or otherwise manage a condition of patient 12. Lead 16 is implanted within patient 12 such that one or more electrodes 17 carried by lead 16 are located proximate to a target tissue site within brain 18. In some examples, more than one lead 16 may be implanted within brain 18 of patient 12 to provide stimulation to multiple tissue sites (e.g., different brain structures) within brain 18. As shown in FIG. 1A, system 10 may also include a programmer 20, which may be a handheld device, portable computer, or workstation that provides a user interface to a clinician or other user. The clinician may interact with the user interface to program stimulation parameter values for IMD 14, which may include, for example, the electrodes 17 that are activated, the polarity of the electrodes 17, a current or voltage amplitude and, in the case of stimulation in the form of electrical pulses, pulse width and pulse rate (or frequency) for stimulation signals to be delivered to patient 12.

DBS may be used to treat or manage various patient conditions, such as, but not limited to, seizure disorders (e.g., epilepsy), pain, migraine headaches, psychological disorders (e.g., an anxiety disorder, major depressive disorder, bipolar disorder, and the like), movement disorders (e.g., essential tremor or Parkinson's disease), Huntington's disease, and other neurodegenerative disorders. During implantation of lead 16 within patient 12, a clinician may attempt to position electrodes 17 of lead 16 close to or within a target anatomical region. The anatomical region within patient 12 that serves as the target tissue site for stimulation delivered by IMD 14 may be selected based on the patient condition. For example, stimulating particular structures of brain 18, such as the Substantia Nigra, may help reduce the number and magnitude of tremors experienced by patient 12. Other anatomical regions for DBS may include the subthalamic nucleus, globus pallidus interna, ventral intermediate, and zona inserta.

While DBS may successfully reduce symptoms of some neurological diseases, the stimulation may also cause unwanted side effects. Side effects may include incontinence, tingling, loss of balance, paralysis, slurred speech, loss of memory, loss of inhibition, and many other neurological problems. Side effects may be mild to severe. DBS may cause one or more side effects by inadvertently providing electrical stimulation to anatomical regions near the targeted anatomical region. For this reason, the clinician typically programs the stimulation parameter values in order to balance effective therapy and minimal side effects. As described in further detail below, the clinician, with the aid of a computing device, such as programmer, may generate an algorithmic model of a baseline therapy field based on the stimulation parameter values, the patient's anatomy, and tissue characteristics of the target anatomical region. The algorithmic model of the baseline therapy field may indicate the electrical field, activation field, voltage gradient or current density of electrical stimulation that balances effective therapy and minimal side effects. A departure from the baseline therapy field may result in less efficacious therapy to patient 12, an increase in undesired side effects, or a combination thereof.

DBS lead 16 may include one or more electrodes 17 placed along the longitudinal axis of lead 16. In some examples, electrodes 17 may include at least one ring electrode that resides along the entire circumference of lead 16. Electrical current from a ring electrode propagates in all directions from the active electrode. The resulting stimulation field reaches anatomical regions of brain 18 within a certain distance in all directions. The stimulation field may reach the target anatomical region, but the stimulation field may also affect non-target anatomical regions and produce unwanted side effects.

In other examples, electrodes 17 of lead 16 may include a complex electrode array geometry that includes segmented or partial ring electrodes in addition to or instead of ring electrodes. The electrodes in a complex electrode array may be located at different axial positions and angular positions around the circumference of the lead, as well as at different longitudinal positions (e.g., substantially along a longitudinal axis of a lead body). A complex electrode array geometry may be useful for customizing the stimulation field and provide improved therapy while decreasing side effects. For example, with a complex electrode array, electrodes may be selected along the longitudinal axis of lead 16 and along the circumference of lead 16. Activating selective electrodes of lead 16 can produce customizable stimulation fields that may be directed to a particular side of lead 16 in order to isolate the stimulation field around the target anatomical region of brain 18. In this manner, specific electrodes of the complex electrode array geometry may be selected to produce a stimulation field at desired portions of the circumference instead of always producing a stimulation field around the entire circumference of the lead, as with some ring electrodes.

While both ring electrodes and a complex electrode geometry may provide efficacious therapy to patient 12, in some cases, producing irregular stimulation fields with a lead 16 with a complex electrode geometry may allow therapy system 10 to more accurately and precisely target certain anatomical regions of brain 18 compared to a lead 16 with ring electrodes. In addition, therapy system 10 including a complex electrode geometry may also reduce or eliminate side effects from more spherical stimulation fields produced by a conventional array of ring electrodes. The center of the stimulation field may be moved away from lead 16 to avoid unwanted stimulation or compensate for inaccurately placed leads.

In the example shown in FIG. 1A, lead 16 is coupled to IMD 14 via connector 22, which defines a plurality of electrical contacts for electrically coupling electrodes 17 to a stimulation generator within IMD 14. Lead 16 is indirectly coupled to connector 22 with the aid of lead extension 24. In some examples, lead 16 may be directly coupled to connector 22 without the aid of extension 24.

Programmer 20 is an external computing device that is configured to wirelessly communicate with IMD 14. For example, programmer 20 may be a clinician programmer that the clinician uses to communicate with IMD 14. Alternatively, programmer 20 may be a patient programmer that allows patient 12 to view and modify therapy parameter values. The clinician programmer may include more programming features than the patient programmer. In other words, more complex or sensitive tasks may only be allowed by the clinician programmer to prevent patient 12 from making undesired changes to IMD 14.

Programmer 20 may be a hand-held computing device that includes a display viewable by the user (e.g., a clinician or patient 12) and a user input mechanism that can be used to provide input to programmer 20. For example, programmer 20 may include a small display screen (e.g., a liquid crystal display or a light emitting diode display) that presents information to the user. In addition, programmer 20 may include a keypad, buttons, a peripheral pointing device, touch screen or another input mechanism that allows the user to navigate though the user interface of programmer 20 and provide input.

If programmer 20 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 20 may be a touch screen that allows the user to provide input directly to the user interface shown on the display. The user may use a stylus or their finger to provide input to the display.

In other examples, rather than being a handheld computing device or a dedicated computing device, programmer 20 may be a larger workstation or a separate application within another multi-function device. For example, the multi-function device may be a cellular phone or personal digital assistant that is configured to run an application that simulates one or more functions of programmer 20. Alternatively, a notebook computer, tablet computer, or other personal computer may run an application that enables the computer to function as programmer 20. A wireless adapter may be connected to the personal computer to enable to computer to securely communicate with IMD 14.

When programmer 20 is configured for use by the clinician, programmer 20 may be used to transmit initial programming information to IMD 14. This initial information may include hardware information of therapy system 10, such as the type of lead 16, the position of lead 16 within patient 12, the therapy parameter values of therapy programs stored within IMD 14 or within programmer 20, and any other information the clinician desires to program into IMD 14.

With the aid of programmer 20 or another computing device, a clinician may select values for therapy parameter values for therapy system 10. The therapy parameter values may be organized into a group referred to as a "therapy program." In the case of electrical stimulation, the therapy parameters may include an electrode combination, and an amplitude, which may be a current or voltage amplitude, a pulse width, and a pulse rate (or frequency) for stimulation signals to be delivered to the patient. An electrode combination may include a selected subset of one or more electrodes 17 located on one or more implantable leads 16 coupled to IMD 14. The electrode combination may also refer to the polarities of the electrodes in the selected subset. By selecting particular electrode combinations, a clinician may target particular structures within brain 18. In addition, by selecting values for amplitude, pulse width, and pulse rate, the clinician may generate an efficacious therapy for patient 12 that is delivered via the selected electrode subset. Due to physiological diversity, condition differences, and in accuracies in lead placement, the parameter values may vary between patients.

During a programming session, the clinician may determine stimulation parameter values for one or more therapy programs that provide effective therapy to patient 12. Patient 12 may provide feedback to the clinician as to the efficacy of the specific program being evaluated. Once the clinician has identified one or more programs that may be beneficial to patient 12, patient 12 may continue the evaluation process and determine which program best alleviates the condition of patient 12 or otherwise provides efficacious therapy to patient 12. Programmer 20 may assist the clinician in the creation/identification of therapy programs by providing a user interface that implements a methodical system of identifying potentially beneficial therapy parameter values.

In some examples, the clinician may select therapy parameter values using the techniques described in commonly-assigned U.S. patent application Ser. No. 11/591,299 to Stone et al., entitled, "ELECTRICAL AND ACTIVATION FIELD MODELS FOR CONFIGURING STIMULATION THERAPY" and filed on Oct. 31, 2006, and commonly-assigned U.S. patent application Ser. No. 11/591,188 to Goetz et al., entitled, "PROGRAMMING INTERFACE WITH A CROSS-SECTIONAL VIEW OF A STIMULATION LEAD WITH COMPLEX ELECTRODE ARRAY GEOMETRY," and filed on Oct. 31, 2006. U.S. patent application Ser. Nos. 11/591,299 and 11/591,188 describe programming systems and methods that support the programming of stimulation parameter values with a therapy system 10 including a lead 16, which may include a complex electrode array geometry.

In accordance with techniques described in U.S. patent application Ser. No. 11/591,299 to Stone et al., a user interface of programmer 20 may display a representation of the anatomical regions of patient 12, specifically anatomical regions of brain 18. The three-dimensional (3D) space of the anatomical regions may be displayed as multiple two-dimensional (2D) views or a 3D visualization environment. Lead 16 may also be represented on the display of the user interface and positioned relative to the representation of brain 18 shown on the display of programmer 20 according to the actual implantation location by the clinician or directly from an image taken of the lead within brain 18. The clinician may interact with the user interface of programmer 20 to manually select and program certain electrodes of lead 16, adjust the resulting stimulation field with the anatomical regions as guides or define one or more stimulation fields that only affect anatomical regions of interest. Once the clinician has defined the one or more stimulation fields, system 10 may automatically generate the stimulation parameter values associated with each of the stimulation fields and transmits the parameter values to IMD 14.

In accordance with techniques described in U.S. patent application Ser. No. 11/591,188 to Goetz et al., programmer 20 may present a user interface that displays electrodes of lead 16 and enables a user to select individual electrodes to form an electrode combination and specify parameter values for stimulation delivered via the electrode combination. In accordance with other techniques described in U.S. patent application Ser. No. 11/591,188 to Goetz et al., programmer 20 may present a user interface to a user that enables the user to manipulate a representation of an electrical stimulation field (i.e., one type of therapy field) produced by a selected electrode combination. A processor within programmer 20 may then select the appropriate electrode combination, electrode polarities, amplitudes, pulse widths, and pulse rates of electrical stimulation sufficient that best fit a stimulation field created by a user via a user interface of programmer 20.

Programmer 20 may also be configured for use by patient 12. When configured as the patient programmer, programmer 20 may have limited functionality in order to prevent patient 12 from altering critical functions or applications that may be detrimental to patient 12. In this manner, programmer 20 may only allow patient 12 to adjust certain therapy parameter values or set an available range of values for a particular therapy parameter. Programmer 20 may also provide an indication to patient 12 when therapy is being delivered or when IMD 14 or when the power source within programmer 20 or IMD 14 need to be replaced or recharged.

Whether programmer 20 is configured for clinician or patient use, programmer 20 may communicate to IMD 14 or any other computing device via wireless communication. Programmer 20, for example, may communicate via wireless communication with IMD 14 using radio frequency (RF) telemetry techniques known in the art. Programmer 20 may also communicate with another programmer or computing device via a wired or wireless connection using any of a variety of local wireless communication techniques, such as RF communication according to the 802.11 or Bluetooth specification sets, infrared communication according to the IRDA specification set, or other standard or proprietary telemetry protocols. Programmer 20 may also communicate with another programming or computing device via exchange of removable media, such as magnetic or optical disks, or memory cards or sticks. Further, programmer 20 may communicate with IMD 14 and other another programmer via remote telemetry techniques known in the art, communicating via a local area network (LAN), wide area network (WAN), public switched telephone network (PSTN), or cellular telephone network, for example.

In other applications of therapy system 10, the target therapy delivery site within patient 12 may be a location proximate to a spinal cord or sacral nerves (e.g., the S2, S3 or S4 sacral nerves) in patient 12, or any other suitable nerve, organ, muscle or muscle group in patient 12, which may be selected based on, for example, a patient condition. For example, therapy system 10 may be used to deliver electrical stimulation to tissue proximate to a pudendal nerve, a perineal nerve or other areas of the nervous system, in which cases, lead 16 would be implanted and substantially fixed proximate to the respective nerve. As further examples, an electrical stimulation system may be positioned to deliver a stimulation to help manage peripheral neuropathy or post-operative pain mitigation, ilioinguinal nerve stimulation, intercostal nerve stimulation, gastric stimulation for the treatment of gastric mobility disorders and obesity, muscle stimulation, for mitigation of other peripheral and localized pain (e.g., leg pain or back pain). In addition, although a single lead 16 is shown in FIG. 1A, in some therapy systems, two or more leads may be electrically coupled to IMD 14.

Figure 1B:
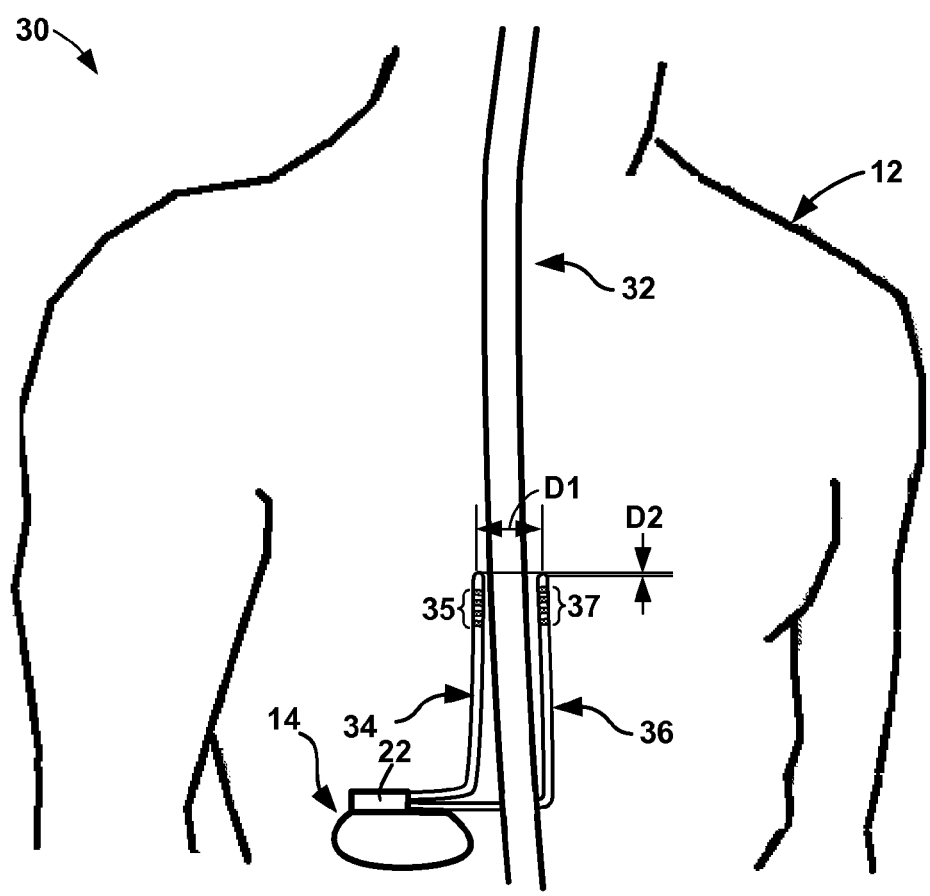

FIG. 1B is a conceptual diagram of another example of therapy system 30 that delivers electrical stimulation to target tissue sites proximate to spine 32 of patient 12. Therapy system 30 includes IMD 14, which is coupled to leads 34, 36 via connector 22. Leads 34, 36 each include an array of electrodes 35, 37, respectively. IMD 14 may deliver stimulation to patient 12 via a combination of electrodes 35, 37. Electrodes 35, 37 may each be any suitable type of electrode, such as a ring electrode, partial ring electrode or segmented electrode.

In some examples, electrodes 17 (FIG. 1A), 35, 37 may also include at least one sense electrode that senses a physiological parameter of patient 12, such as, but not limited to, a heart rate, respiration rate, respiratory volume, core temperature, muscular activity, tissue impedance, electromyogram (EMG), an electroencephalogram (EEG) or electrocorticogram (ECoG), an electrocardiogram (ECG) or galvanic skin response. Therapy systems 10, 30 may include sensor 26, which may be a sensor configured to detect an activity level, posture, or a physiological parameter of patient 12. Sensor 26 may be implanted or external to patient 12, and may be wirelessly coupled to IMD 14 or via a lead, such as leads 16, 34, 36, or another lead. For example, sensor 26 may be implanted within patient 12 at a different site than IMD 14 or sensor 26 may be external. In addition or instead of being coupled to IMD 14, in some cases, sensor 26 may be wirelessly coupled to programmer 20 or coupled to programmer 20 by a wired connection.

In the example shown in FIG. 1B, leads 34, 36 are positioned to deliver bilateral stimulation to patient 12, i.e., stimulation signals are delivered to target tissue sites on opposite sides of a midline of patient 12. The midline may be generally defined by spinal cord 32. A distance between leads 34, 36, and, more specifically, a distance between electrodes 35, 37 of leads 34, 36 may affect the therapy field that results from electrical stimulation delivered by IMD 14 according to a therapy program. For example, the further apart electrodes 35, 37 are spaced from each other in either or both the left/right (laterally) direction or the dorsal/ventral direction (distance D1, shown schematically in FIG. 1B) or in the superior-inferior direction (distance D2, shown schematically in FIG. 1B), the less overlap there may be in stimulation propagating from electrodes 35, 37, which may affect the neurons that are activated by the electrical field. Distance D1 may be measured, e.g., from a longitudinal axis of lead 34 to a longitudinal axis of lead 36, and may traverse more than one direction, i.e., may extend both laterally, in a left/right direction and in a dorsal/ventral direction. Distance D2 may be measured, e.g., from the distal end of lead 34 to the distal end of lead 36. As another example, if one or both of leads 34 and 36 move, the electrodes 35 and 37 may shift and the centroid of stimulation may change, which may affect the efficacy of therapy.

Just as with therapy system 10, a clinician may generate one or more therapy programs for therapy system 30 by selecting values for a plurality therapy parameters that provide efficacious therapy to patient 12 with the aid of programmer 20 or another computing device. The therapy parameters may include for example the combination of the electrodes of lead 16, the voltage or current amplitude, pulse width, and frequency of stimulation.

For therapy system 10 (FIG. 1A), therapy system 30 (FIG. 1B) or any other therapy system that provides electrical stimulation therapy to patient 12 to patient 12, an algorithmic model of a baseline therapy field that provides efficacious therapy to patient 12 may be generated with the aid of modeling software, hardware or firmware executing on a computing device, such as programmer 20 or a separate dedicated or multifunction computing device. The algorithmic model of the baseline therapy (also referred to as a "baseline therapy field model") may be stored within a memory of programmer 20, IMD 14 or another device. The algorithmic model of the baseline therapy field is a known therapy field that results from delivery of stimulation according to at least one therapy program determined to deliver efficacious therapy to the patient, and is also based on the patient's anatomy, such as the tissue characteristics at the target tissue site (e.g., the impedance of the tissue).

While the remainder of the description of FIGS. 2-6 primarily refers to therapy system 30 of FIG. 1B, in other examples, the techniques for generating an algorithmic model of a baseline therapy field and modifying a therapy program based information indicative of a change in a therapy field may be applied to therapy system 10 of FIG. 1A that provides DBS to patient 12. In addition, while the remainder of the description primarily refers to an algorithmic model of a baseline therapy field that is generated with the aid of modeling software executing on a computing device, in other examples, the algorithmic model of a baseline therapy field may be generated with the aid of hardware or firmware.

In some examples, the modeling software implements an algorithm that models the therapy field based on an anatomy of patient 12, the therapy program determined to provide efficacious therapy to patient 12, and the hardware characteristics of therapy system 10 or therapy system 30. In the case of therapy system 30 (FIG. 1B), the hardware characteristics may include the type of IMD 14, the type of leads 34, 36, which may include the type of electrodes 35, 37 (e.g., ring electrodes, partial ring electrodes or segmented electrodes), a baseline impedance of electrodes 35, 37 (i.e., a known impedance of electrodes 35, 37 at the time an efficacious therapy program was selected or an impedance of electrodes 35, 37 indicated by the manufacturer of leads 34, 36), and the baseline impedance presented to IMD 14 at the time of initial programming, i.e., the impedance of the entire path between IMD 14 and the target tissue site, including lead conductors, electrodes 35, 37, and patient tissue through which stimulation travels.

The hardware characteristics of the therapy system may include a baseline distance between the electrodes of the leads. For example, in the case of therapy system 30, the baseline spacing between electrodes 35, 37 of leads 34, 36 may be, for example, the spacing between electrodes 35, 37 at the time of implant of leads 34, 36. The algorithm for generating the baseline therapy model as well as other therapy models may be stored within a memory of programmer 20, IMD 14 or another device.

In examples in which a clinician programs parameter values of IMD 14 by selecting a stimulation field and subsequently generating the stimulation parameter values that result in the selected stimulation field, the baseline therapy field model may be a digital model of the stimulation field selected by the clinician. For example, the algorithmic model of the baseline therapy field may be an electrical field model that is generated based upon patient anatomy data and a therapy program defining stimulation parameter values, where the electrical field model represents the areas of a patient anatomical region that will be covered by an electrical field during therapy. The patient anatomy data may include at least one of an anatomical image of a patient, a reference anatomical image, an anatomical atlas or a tissue conductivity data set. The patient anatomy data may be specific to patient 12 or may represent data for more than one patient, e.g., model or averaged data of the anatomical structure and tissue conductivity of multiple patients. For example, in some examples, the patient anatomy data may include tissue conductivity data or other relevant tissue data that is typical for the particular lead 34, 36 location for the particular therapeutic application (e.g., spinal cord stimulation in the case of FIG. 1B), and may be, but need not be, specific to patient 12.

The electrical field model may represent where electrical stimulation propagates through tissue from electrodes 35, 37 of leads 34, 36. Patient anatomy data may indicate one or more characteristics of patient tissue proximate to an implanted leads 34, 36, and may be created from any type of imaging modality, such as, but not limited to, computed tomography (CT), magnetic resonance imaging (MRI), x-ray, fluoroscopy, and the like.

In other examples, the algorithmic model of the baseline therapy field may be an activation field model that may be based on a neuron model that indicates one or more characteristics of patient neural tissue proximate to implanted leads 34, 36. The activation field may indicate the neurons that will be activated by the electrical field in the anatomical region. The clinician may program the therapy parameter values for IMD 14 by selecting a desired therapy field and generate therapy parameter values that may achieve the desired therapy field, taking into consideration the patient's anatomy and the hardware characteristics of therapy system 10. As previously indicated, the hardware characteristics may include the type of IMD 14, the type of leads 34, 36 implanted within patient 12, the type of electrodes 35, 37, and, if applicable, the spacing between the leads and/or electrodes of different leads within patient 12.

In other examples, an algorithmic model of the baseline therapy field may be generated after selecting therapy parameter values. For example, the clinician may select therapy parameter values that provide efficacious therapy to patient 12 and generate an algorithmic model of the therapy field resulting from the therapy parameter values with the aid of modeling software executing on a computing device, such as programmer 20 or a separate workstation or computing device. Again, the resulting therapy field may be based on an algorithmic model that is based on the therapy parameter values, the patient's anatomy, and the hardware characteristics of therapy system 10.

In yet other examples, the algorithmic model of the baseline therapy field may be a therapy field model that is known to manage the patient's condition, and may not be specific to the particular patient 12. For example, the baseline therapy field may be a part of a therapy model stored within programmer 20 or another computing device, where the therapy model provides guidelines as to therapy fields that have been shown (e.g., by clinical studies or computer modeling) to address the patient's condition. The therapy model may, for example, indicate the particular anatomical structures within brain 18 that should be activated by an electrical field in order to manage the patient's condition.

Figure 2:
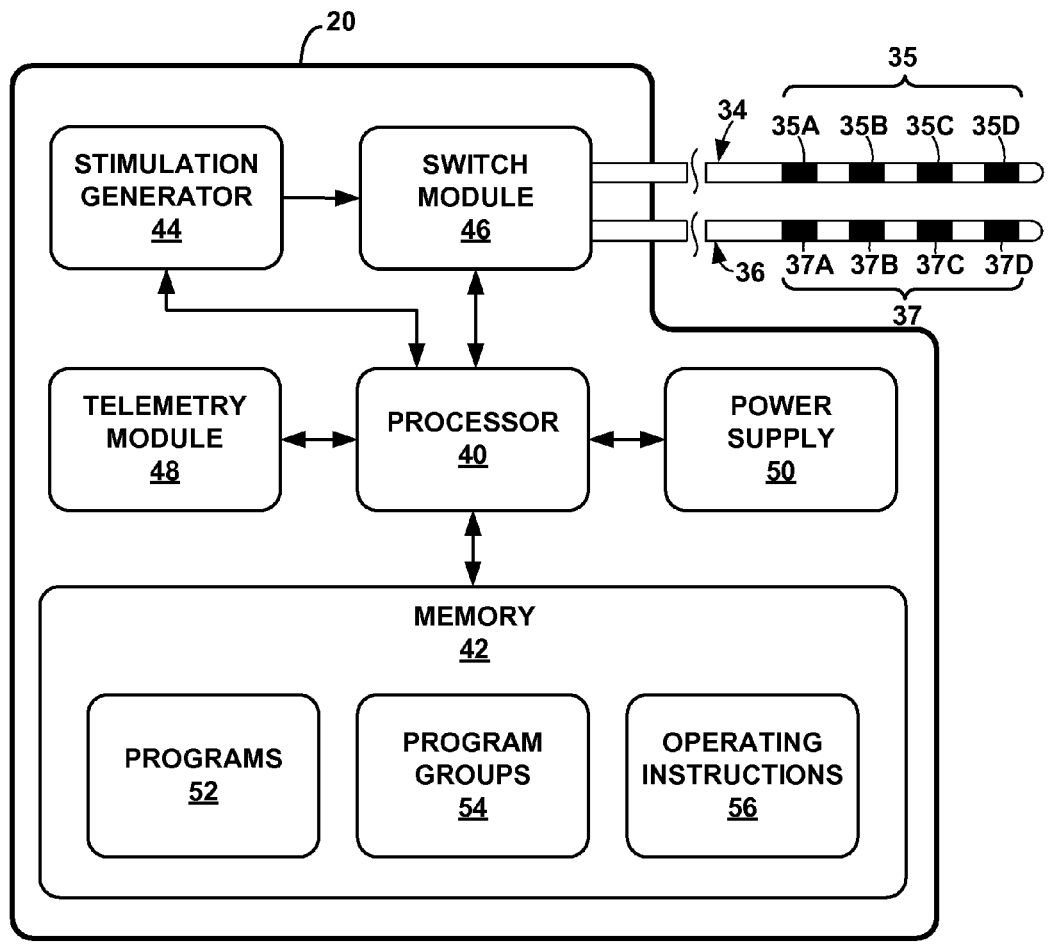
FIG. 2 is a functional block diagram of an example implantable medical device that generates electrical stimulation signals.

FIG. 2 is a functional block diagram of an example IMD 14. IMD 14 includes a processor 40, memory 42, stimulation generator 44, switch module 46 (or switching module), telemetry module 48, and power source 50. As shown in FIG. 2, stimulation generator 44 is coupled to leads 34, 36. Alternatively, stimulation generator 44 may be coupled to a single lead (e.g., as shown in FIG. 1A) or three or more leads, either directly or indirectly (e.g., via a lead extension, such as a bifurcating lead extension that may electrically and mechanically couple to two leads) as needed to provide stimulation therapy to patient 12.

In the example illustrated in FIG. 2, lead 34 includes electrodes 35A-35D (collectively referred to as "electrodes 35") and lead 36 includes electrodes 37A-37D (collectively referred to as "electrodes 37"). Electrodes 35, 37 may be ring electrodes. In other examples, electrodes 35, 37 may be arranged in a complex electrode array that includes multiple non-contiguous electrodes at different angular positions about the outer circumference of the respective lead 34, 36. The configuration, type, and number of electrodes 35, 37 illustrated in FIG. 2 are merely exemplary. In other examples, IMD 14 may be coupled to any suitable number of leads with any suitable number and configuration of electrodes.

Memory 42 includes computer-readable instructions that, when executed by processor 40, cause IMD 14 to perform various functions. Memory 42 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Memory 42 may include programs 52, program groups 54, and operating instructions 56 in separate memories within memory 42 or separate areas within memory 42. Each program 52 defines a particular program of therapy in terms of respective values for electrical stimulation parameters, such as electrode combination, electrode polarity, current or voltage amplitude, pulse width and pulse rate. A program group 54 defines a group of programs that may be delivered together on an overlapping or non-overlapping basis. Operating instructions 56 guide general operation of IMD 14 under control of processor 40, and may include instructions for measuring the impedance of electrodes 35, 37 and/or determining the distance between electrodes 35, 37.

Stimulation generator 44 produces stimulation signals, which may be pulses as primarily described herein, or continuous time signals, such as sine waves, for delivery to patient 12 via selected combinations of electrodes 35, 37. Processor 40 controls stimulation generator 44 according to programs 52 and program groups 54 stored in memory 42 to apply particular stimulation parameter values specified by one or more of programs, such as amplitude, pulse width, and pulse rate. Processor 40 may be provided by any one or more of a microprocessor, a controller, a digital signal processor (DSP), an application specific integrated circuit (ASIC), a field-programmable gate array (FPGA), or equivalent discrete or integrated digital or analog logic circuitry, and functions attributed to processor 40 herein may be embodied as software, firmware, hardware or any combination thereof.

Processor 40 also controls switch module 46 to apply the stimulation signals generated by stimulation generator 44 to selected combinations of electrodes 35, 37. In particular, switch module 46 couples stimulation signals to selected conductors within leads 34, 36 which, in turn, deliver the stimulation signals across selected electrodes 35, 37. Switch module 46 may be a switch array, switch matrix, multiplexer, or any other type of switching module suitable to selectively couple stimulation energy to selected electrodes. Hence, stimulation generator 44 is coupled to electrodes 35, 37 via switch module 46 and conductors within leads 34, 36. In some examples, however, IMD 14 does not include switch module 46.

Stimulation generator 44 may be a single channel or multi-channel stimulation generator. In particular, stimulation generator 44 may be capable of delivering, a single stimulation pulse, multiple stimulation pulses or continuous signal at a given time via a single electrode combination or multiple stimulation pulses at a given time via multiple electrode combinations. In some examples, however, stimulation generator 44 and switch module 46 may be configured to deliver multiple channels on a time-interleaved basis. For example, switch module 46 may serve to time divide the output of stimulation generator 44 across different electrode combinations at different times to deliver multiple programs or channels of stimulation energy to patient 12.

Telemetry module 48 supports wireless communication between IMD 14 and an external programmer 20 or another computing device under the control of processor 40. Processor 40 of IMD 14 may receive, as updates to programs, values for various stimulation parameters such as amplitude and electrode combination, from programmer 20 via telemetry interface 48. The updates to the therapy programs may be stored within programs 52 portion of memory 42.

The various components of IMD 14 are coupled to power supply 50, which may include a rechargeable or non-rechargeable battery. A non-rechargeable battery may be selected to last for several years, while a rechargeable battery may be inductively charged from an external device, e.g., on a daily or weekly basis. In other examples, power supply 50 may be powered by proximal inductive interaction with an external power supply carried by patient 12.

Figure 3:
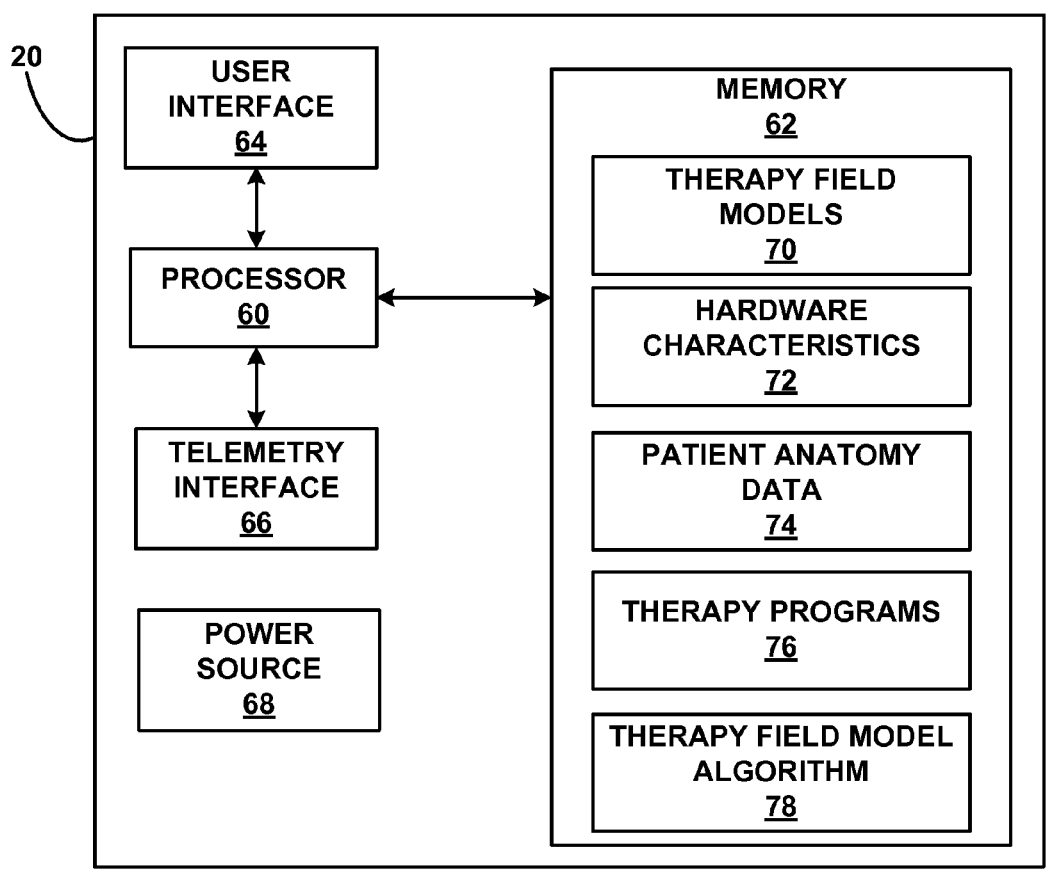
FIG. 3 is a functional block diagram of an example medical device programmer.

FIG. 3 is a functional block diagram of an example programmer 20. As shown in FIG. 3, external programmer 20 includes processor 60, memory 62, user interface 64, telemetry module 66, and power source 68. Memory 62 includes baseline therapy field model 70, hardware characteristics 72, patient anatomy data 74, and therapy programs 76 in separate memories within memory 42 or separate areas within memory 42.

A clinician or another user may interact with programmer 20 to generate and/or select therapy programs for delivery in IMD 14. For example, in some examples, programmer 20 may allow a clinician to define stimulation fields and generate appropriate stimulation parameter values, which may be stored as therapy programs within therapy programs 76 portion of memory 62 or within IMD 14. Programmer 20 may be used to present anatomical regions to the user via user interface 64, select stimulation programs, generate new stimulation programs with stimulation fields, and transmit the new programs to IMD 14, as described in U.S. patent application Ser. No. 11/591,599 to Stone et al. and entitled, "ELECTRICAL AND ACTIVATION FIELD MODELS FOR CONFIGURING STIMULATION THERAPY." Processor 60 may store stimulation parameter values as one or more therapy programs in memory 62. Processor 60 may send programs to IMD 14 via telemetry module 66 to control stimulation automatically and/or as directed by the user.

Programmer 20 may be one of a clinician programmer or a patient programmer in some examples, i.e., the programmer may be configured for use depending on the intended user. A clinician programmer may include more functionality than the patient programmer. For example, a clinician programmer may include a more featured user interface, allowing a clinician to download usage and status information from IMD 14, and allowing a clinician to control aspects of IMD 14 not accessible by a patient programmer.

A user, either a clinician or patient 12, may interact with processor 60 through user interface 64. User interface 64 may include a display, such as a liquid crystal display (LCD), light-emitting diode (LED) display, or other screen, to show information related to stimulation therapy, and buttons or a pad to provide input to programmer 20. In examples where user interface 64 requires a 3D environment, the user interface may support 3D environments such as a holographic display, a stereoscopic display, an autostereoscopic display, a head-mounted 3D display, or any other display that is capable of presenting a 3D image to the user. Buttons may include an on/off switch, plus and minus buttons to zoom in or out or navigate through options, a select button to pick or store an input, and pointing device, i.e. a mouse, trackball or stylus. Other input devices may be a wheel to scroll through options or a touch pad to move a pointing device on the display. In some examples, the display may be a touch screen that enables the user to select options directly from the display screen.

Programmer 20 may be a handheld computing device, a workstation or another dedicated or multifunction computing device. For example, programmer 20 may be a general purpose computing device (e.g., a personal computer, personal digital assistant (PDA), cell phone, and so forth) or may be a computing device dedicated to programming IMD 14.

Processor 60 processes instructions from memory 62 and may store user input received through user interface 64 into the memory when appropriate for the current therapy. In addition, processor 60 provides and supports any of the functionality described herein with respect to each example of user interface 64. Processor 60 may be provided any one or more of a microprocessor, DSP, ASIC, FPGA, or other digital logic circuitry, and may be embodied as software, firmware, hardware or any combinations thereof.

Memory 62 may include instructions for operating user interface 64, telemetry module 66 and managing power source 68. Memory 62 may store program instructions that, when executed by processor 60, cause the processor and programmer 20 to provide the functionality ascribed to them herein. Memory 62 also includes instructions for generating therapy programs, such as instructions for determining stimulation parameter values for achieving a user-selected stimulation fields or instructions for determining a resulting stimulation field from user-selected stimulation parameter values. Memory 62 may include any one or more of a RAM, ROM, EEPROM, flash memory, or the like.

In addition, memory 62 stores algorithmic models of one or more therapy field models 70, which may include a baseline therapy field model. The models of the therapy fields may be generated by processor 60 using an algorithm stored within therapy field model algorithm section 78 of memory 62. The stored algorithm 78 may determine a therapy field model based on the stimulation parameter values of therapy programs 76, the hardware characteristics of therapy system 10 (or therapy system 30) stored within hardware characteristics 72 portion of memory 62, and patient anatomy data 74. As previously indicated, the hardware characteristics may include the type of IMD 14, the type of leads 34, 36, which may include the type of electrodes 35, 37 (e.g., ring electrodes, partial ring electrodes or segmented electrodes), and a baseline impedance of electrodes 35, 37. In examples in which a therapy system includes two or more leads, such as therapy system 30 in FIG. 1B, the hardware characteristics of the therapy system may include a baseline distance between the electrodes of the leads. In addition, the patient anatomy data may include the anatomical structure of patient 12 and the characteristics of the tissue, such as the impedance, proximate to electrodes 35, 37.

Wireless telemetry in programmer 20 may be accomplished by radio frequency (RF) communication or proximal inductive interaction of programmer 20 with IMD 14. This wireless communication is possible through the use of telemetry module 66. Accordingly, telemetry module 66 may include circuitry known in the art for such communication. Power source 68 delivers operating power to the components of programmer 20. Power source 68 may include a battery and a power generation circuit to produce the operating power. In some examples, the battery may be rechargeable to allow extended operation. Recharging may be accomplished through proximal inductive interaction, or electrical contact with circuitry of a base or recharging station. In other examples, primary batteries may be used. In addition, programmer 20 may be directly coupled to an alternating current source, such would be the case with some computing devices, such as personal computers.

Figure 4:
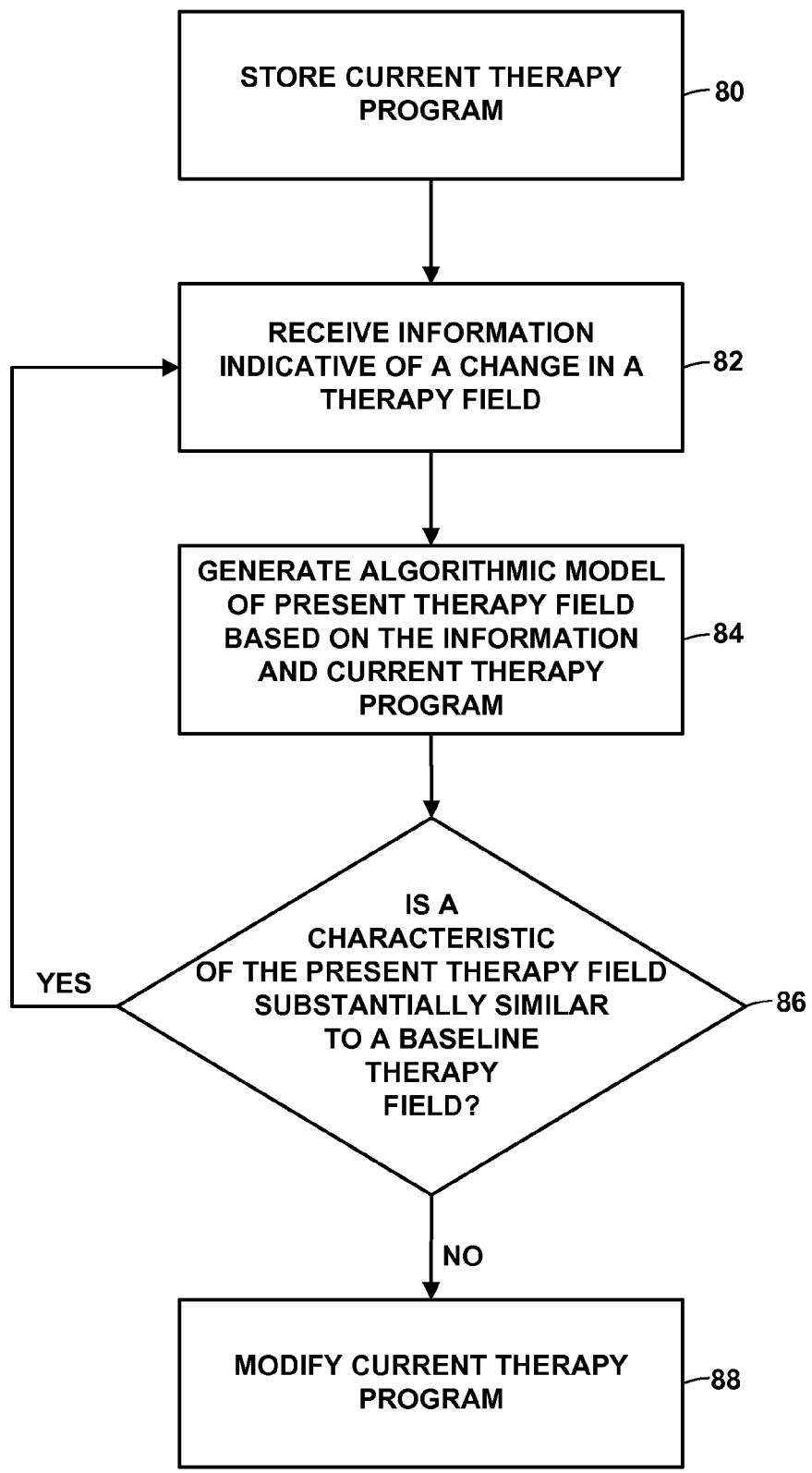
FIG. 4 is a flow diagram illustrating an example technique for modifying a therapy program based on information indicative of a change in a therapy field.
Figure 6:
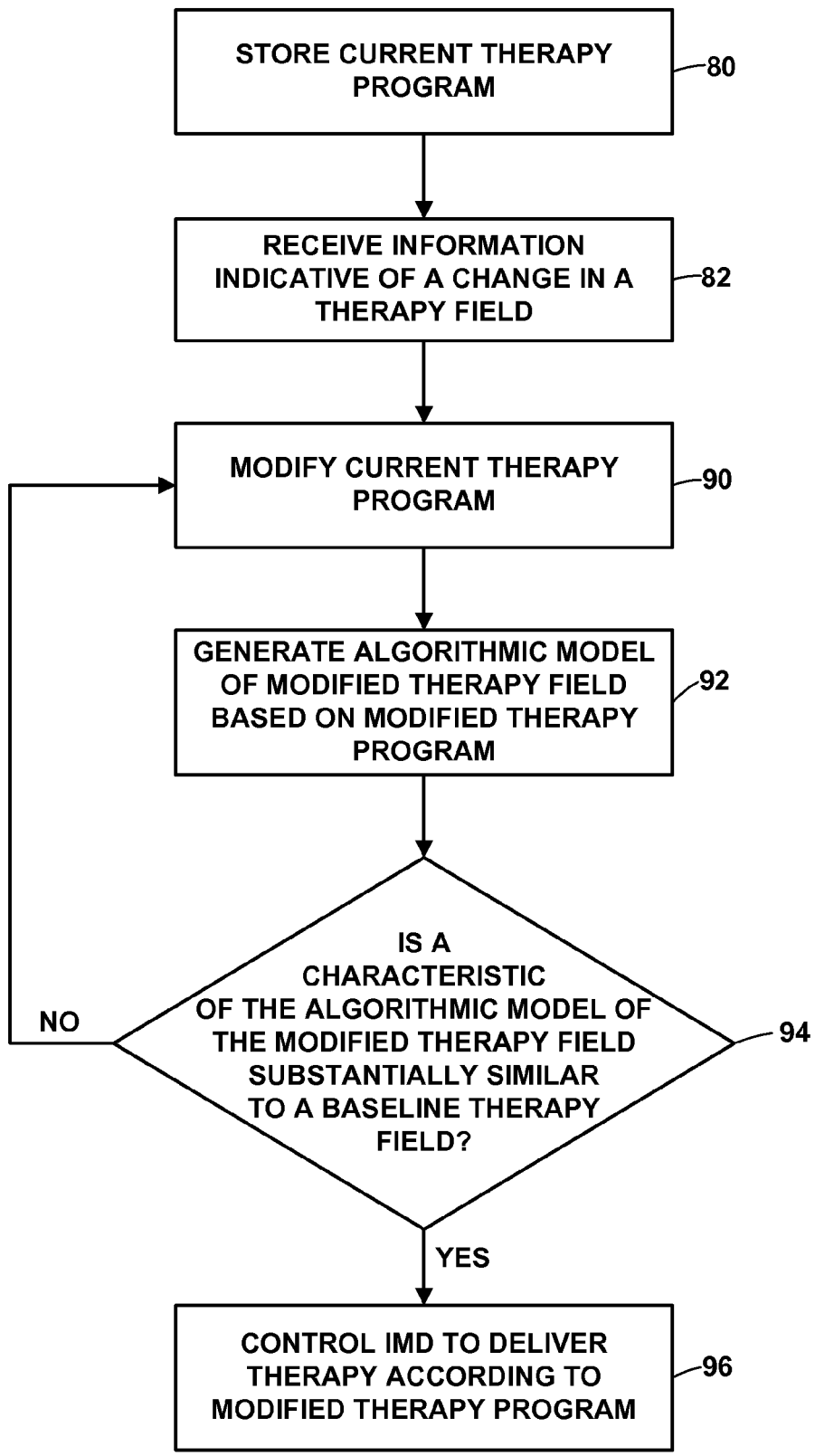
FIG. 6 is a flow diagram illustrating another example technique for modifying a therapy program based on information indicative of a change in a therapy field.

FIGS. 4 and 6 are flow diagrams illustrating examples of techniques for modifying a therapy program based on information indicative of a change in a therapy field. While the therapy program modification techniques shown in FIGS. 4 and 6 are described as being performed by programmer 20, in other examples, processor 40 of IMD 14 or a processor of another computing device, such as a clinician workstation, or any combination of devices may execute the techniques for modifying a therapy program shown in FIGS. 4 and 6.

In the technique shown in FIG. 4, IMD 14 delivers electrical stimulation therapy to patient 12 according to a current therapy program (80). Programmer 20 may store an indication of the current therapy program within therapy programs portion 76 of memory 62 (80). The indication may include the therapy parameter values of the current therapy program or an indicator (e.g., an alphanumeric indicator) associated with the therapy program. Processor 60 may determine the therapy parameter values based on the alphanumeric indicator by referencing a data structure within memory 62 that associates alphanumeric indicators with particular therapy parameter sets or by interrogating IMD 14. Programmer 20 may acquire the indication of the current therapy program by any suitable technique. In one example, a clinician, patient 12 or another user provides input to programmer 20 via user interface 64 (FIG. 3) indicating the current therapy program. In another example, programmer 20 may control IMD 14 to deliver therapy according to the current therapy program and store an indication to identify the current therapy program within memory 62. In another example, programmer 20 may interrogate IMD 14 to determine the current therapy program implemented by IMD 14.

Electrical stimulation delivered by IMD 14 generates a therapy field within patient 12. The therapy field may be an electrical field that indicates areas of the patient's tissue that are covered by an electrical field emanating from electrodes 35, 37 of leads 34, 36 during therapy. Alternatively, the therapy field may indicate an activation field that indicates the neurons that are activated by the electrical field. The therapy field may be based on the therapy parameter values of the current therapy program implemented by IMD 14 and the patient anatomy. For example, depending on the target tissue site for stimulation, an electrical field resulting of stimulation therapy delivered according to a particular therapy program may have a different stimulation volume, a different centroid of stimulation or different activated neurons.

Processor 60 of programmer 20 receives information indicative of a change in a therapy field (82). The information indicative of the change in the therapy field may generally indicate that some event occurred that may result in a therapy field change. The event may be, for example, a change in the hardware characteristics of therapy system 30. For example, the information may indicate a change in the impedance of one or more electrodes 35, 37 of leads 34, 36 or an electrical path including electrodes 35, 37 (e.g., an electrical path including conductors between stimulation generator 44 and one or more electrodes 35, 37), an open-circuit condition of one or more electrodes 35, 37, a detected movement of one or both of the leads 34, 36 or a detected change in spacing between leads, if more than one lead is implanted within patient 12. A change in impedance of one or more electrodes 35, 37 may be measured periodically at predetermined intervals, such as once every one to twenty-four hours, by IMD 14, programmer 20 or another device using any suitable technique. Other impedance measuring frequencies are also contemplated. Example methods for determining the impedance associated with a combination of electrodes may similar to commonly known techniques, such as those described in commonly-assigned U.S. Pat. No. 6,978,171, which issued to Goetz et al. on Dec. 20, 2005. As other examples of information indicative of a change in a therapy field, the information may indicate a change within IMD 14, such as a stimulation generator 44 or switch module 46 fault.

Information indicative of a change in a therapy field may also include information indicating a change in the total energy consumed by IMD 14 to generate and deliver electrical stimulation signals according to the current therapy program. In some examples, IMD 14 is configured to generate and deliver electrical stimulation signals having a constant voltage. Accordingly, if the total energy consumed by IMD 14 increases over time, the increased energy may indicate that leads 34, 36 have shifted or the electrical current has increased in order to compensate for an increased impedance between the stimulation generator 44 and target tissue site, e.g., because of tissue ingrowth around electrodes 35, 37 of leads 34, 36, respectively.

Processor 60 of programmer 20 may periodically monitor the energy consumed by IMD 14 to generate and deliver electrical stimulation therapy according to the current therapy program, e.g., by monitoring the available power of power supply 50 (FIG. 2). For example, processor 60 may determine the average consumed energy over a period of time (e.g., an hour up to days), which may be selected by the clinician, or may be predetermined, e.g., by the manufacturer of IMD 14. Processor 40 may determine that the therapy field has changed, e.g., based on a comparison between the consumed energy and a threshold energy level. The threshold energy level may be the energy level at which IMD 14 is no longer operating efficiently, and, therefore, a therapy program change is desirable. The threshold energy level may be stored within memory 62 of programmer 20 (e.g., within hardware characteristics portion 72 of memory 62).

In other examples, IMD 14 may be configured to deliver electrical stimulation signals having a constant current. Accordingly, if the total energy consumed by IMD 14 increases over time, the increased energy may indicate that leads 34, 36 have shifted or the total voltage level has increased in order to compensate for an increased impedance between the stimulation generator 44 and target tissue site.

In other examples, information indicative of a change in a therapy field may also include information indicating a change in the total energy delivered by IMD 14 when IMD 14 delivers therapy according to the current therapy program.

The change in total energy delivered may indicate that, for example, electrodes 35, 37 have shifted or IMD 14 hardware characteristics have changed. Examples of IMD 14 hardware characteristics may include, for example, an energy output of IMD 14 or a channel of IMD 14. As the power source of IMD 14 is depleted, the energy output IMD 14 is capable of generating may decrease, which may affect the therapeutic energy delivered by IMD.

A change in the tissue characteristics proximate to electrodes 35, 37 of leads may also indicate a change in a therapy field. For example, data, such as those provided by functional MRI (fMRI) may provide information indicative of a change in the tissue recruited by therapy delivery according to the current therapy program. As described in further detail below with reference to FIG. 6, in some examples, the information indicative of a change in a therapy field may include information indicating that the therapeutic efficacy of the current therapy program has decreased, thereby suggesting a change in the therapy field.

Processor 60 of programmer 20 may generate an algorithmic model of a therapy field based on the current therapy program (hereinafter referred to as a "present therapy field") and the information indicative of the change in a therapy field (84). The current therapy program may be the therapy program with which IMD 14 is currently delivering stimulation to patient 12, e.g., the most recently selected therapy program. Accordingly, the present therapy field may be the therapy field that is currently generated within patient 12 from the delivery of therapy by IMD 14 according to the current therapy program.

The algorithmic model of the present therapy field may be generated using the same or a different algorithm used to generate the algorithmic model of the baseline therapy field, and the algorithm may be stored within algorithm section 78 of memory 62 (FIG. 3). For example, the algorithmic model of the present therapy field may be based on an anatomy of patient 12, the therapy program determined to provide efficacious therapy to patient 12, and the hardware characteristics of therapy system 10. If the information indicative of a change in a therapy field indicates a change in the hardware characteristics of therapy system 10 or in the tissue characteristics of the tissue at the target tissue site, processor 60 may store the change within hardware characteristics section 72 of memory 62 (FIG. 3) and the new tissue characteristics within patient anatomy data section 74, and generate the algorithmic model of the present therapy field using the modified hardware characteristics. An example of a technique for generating the algorithmic model of the present therapy field is described with respect to FIG. 18.

At least one field characteristic of the algorithmic model of the present therapy field model is compared to a respective characteristic of the algorithmic model of the baseline therapy field model (86). The field characteristics of the therapy fields may include, but are not limited to, centroids of stimulation, the total volumes or cross-sectional areas of the electrical field or activation field, the regions of the patient anatomy recruited or otherwise covered by the therapy field, a charge density or an amplitude of the voltage or current at a certain point within the stimulation therapy field, e.g., whether the voltage or current amplitude at a certain point within the stimulation therapy field exceeds the activation energy of the neurons. The one or more compared characteristics may be selected based on the characteristics of the therapy field that may affect the efficacy of therapy. In addition, the field characteristics may be weighted based on their impact on the efficacy of therapy, and the comparison between the algorithmic models of the present therapy field and the baseline therapy field may be made on the weighted characteristics.

For example, in the case of DBS delivered by therapy system 10 (FIG. 1A), the regions of the patient anatomy recruited or otherwise covered by the therapy field may affect the efficacy of therapy more than the total volume of the electrical field or activation field. Thus, processor 60 may compare the regions of patient anatomy recruited or otherwise covered by the algorithmic model of the present therapy field with the regions of patient anatomy recruited or otherwise covered by the algorithmic model of the baseline therapy field in order to determine whether the current therapy program should be modified. However, in some cases, processor 60 may compare both the regions of patient anatomy recruited by the present therapy field as well as the total volumes of the electrical field or activation field with the respective characteristics of the baseline therapy field model. In the case of spinal cord stimulation delivered by therapy system 30 (FIG. 1B), the centroid of stimulation may affect the efficacy of therapy more than the total volume of the electrical field or activation field. Thus, processor 60 may compare the centroid of stimulation of the algorithmic model of the present therapy field with the centroid of stimulation of the algorithmic model of the baseline therapy field in order to determine whether the current therapy program should be modified. Again, processor 60 may compare more than one field characteristics of the present therapy field model with the baseline therapy field model.

If the one or more characteristics of the present therapy field model or the weighted characteristics do not substantially differ from the baseline therapy field model, processor 60 of programmer 20 may not take any action until further information indicative of a change in a therapy field is received (82). Thus, IMD 14 may continue delivering therapy according to the current therapy program if the comparison between the current and baseline therapy field models indicate, for example, that the change in the therapy field does not significantly affect the efficacy of therapy delivered to patient 12 by the current therapy program, and, therefore, the therapy program does not need to be modified. In some cases, processor 60 may store the received information indicative of the change in the therapy field in memory 62 for later analysis by a clinician.

On the other hand, if the comparison between the current and baseline therapy field models indicates that the present therapy field differs from the baseline therapy field, processor 60 modifies the current therapy program (88). The threshold difference between the at least one characteristic of the current and baseline therapy field models to trigger a modification of the current therapy program may be set by a clinician. For example, in the case of a difference in a volume of an electrical field, processor 60 of programmer 20 may modify the current therapy program upon determining that a volume of a current electrical field model and a volume of a baseline therapy field model differ by at least 10 percent (%), although other percentages are contemplated. Alternatively, processor 60 may modify the current therapy program upon determining that a volume of a current electrical field model is at least 10% smaller than a volume of a baseline therapy field model.

With respect to the centroid of stimulation characteristic of a therapy field, processor 60 of programmer 20 may modify the current therapy program upon determining that a centroid of a current electrical field model has shifted by at least approximately 0.5 millimeters (mm) to about 3 mm relative to a centroid of the baseline electrical field model. In the case of a comparison between the regions of patient anatomy recruited or otherwise covered by the current and baseline therapy fields, processor 60 may modify the current therapy program upon determining that the algorithmic model of the present therapy field indicates that key structures of brain 18 are no longer recruited, where the key structures of brain 18 may be the structures of brain 18 recruited by the algorithmic model of the baseline therapy field. Prior to implementing the modified therapy program, processor 60 may prompt patient 12 and/or a clinician to approve the change.

Other thresholds for triggering a modification of the current therapy program are contemplated, and may differ based on the hardware characteristics of therapy system 10, the target tissue site for therapy delivery or the patient condition. Some patient conditions, such as neurological disorders, may be more affected by a shift in a centroid of stimulation or a change in electrical field volume than other patient conditions, such as chronic pain managed by spinal cord stimulation.

Processor 60 may modify the current therapy program using any suitable technique. In one example, processor 60 may select another therapy program that may be stored in therapy programs section 76 of programmer memory 62, in memory 42 of IMD 14 or a memory of another device. For example, processor 60 may select another therapy program from a set of programs determined to provide efficacious therapy to patient 12. The therapy programs may be ranked in order of efficacy or side effects, and processor 60 may select the next best therapy program.

As another example of a technique for modifying a current therapy program, processor 60 may select the alternative therapy program from a list of stored therapy programs based on a set of rules. In one example, the alternative therapy program may be associated with the information indicative of the change in the therapy field. For example, if the information indicative of the change in the therapy field indicates that a particular electrode of one or both electrode arrays 35, 37 is faulty, processor 60 may determine that the faulty electrode should not be used and select an alternative therapy program based on the faulty electrode, which is no longer available for therapy delivery. An electrode 35, 37 may be determined to be faulty because, for example, a conductor coupling the electrode to switch module 46 has become shorted or otherwise compromised, or because of a change in impedance. Processor 60 may select a therapy program that achieves a therapy field substantially similar to the baseline therapy field (i.e., exactly the same therapy field or exhibiting characteristics within a particular range of the baseline therapy field).

Figure 5:
FIG. 5 is an example data structure that may be referenced to modify a therapy program.

In one example, processor 60 may reference a look-up table stored in memory 62, such as table 88 shown in FIG. 5, or another data structure that provides alternative therapy programs in the event that the particular electrode is unavailable for delivering stimulation. Look-up table 88 associates a faulty electrode with a modified therapy program. In the table 88, the modified therapy programs are given alphanumeric identifiers ("therapy program A," "therapy program B," etc.). However, in other examples, table 88 may list the actual therapy parameter values for the program, rather than a therapy program identifier. If processor 60 determines that electrode 35A is faulty (e.g., based on information, such as electrode impedance, transmitted by IMD 14), processor 60 may select therapy program A. Similarly, if processor determines that electrode 35B is faulty, processor 60 may select therapy program B, and so forth for the other electrodes.

Table 88 illustrated in FIG. 5 associates simple faulty electrode scenarios with suitable alternative therapy programs, whereby only one faulty electrode is associated with an alternative therapy program. In some cases, however, more than one electrode 35, 37 may become faulty after implantation within patient 12. Thus, table 88 may associate different permutations of faulty electrodes with modified therapy programs. A clinician or other user or entity, e.g., a manufacturer of one or more components of therapy system 10, may determine the modified therapy programs that are stored in table 88 based on trialing the combinations, computer-modeling techniques that model a resulting therapy field with modeling scenario in which the particular electrode(s) are faulty or any other suitable method.

In other example, processor 60 may reference a data structure that, e.g., includes an ordered list of therapy programs. Based on the information indicative of a change in a therapy field, processor 60 may select the next-best program that can be delivered as intended, given any changes in hardware indicated by the information indicative of the change in the therapy field.

In another example, processor 60 may modify the current therapy program by generating a new therapy program or modifying at least one parameter value of the current therapy program. Processor 60 of programmer 20 may initiate a programming session with patient 12 after determining that at least one characteristic of a present therapy field model differs from a baseline therapy field model and reference the set of rules to generate a modified therapy program. In one example, processor 60 implements a goal-seeking function, such as to generate a therapy program that results in a therapy field with at least one field characteristic (e.g., a particular stimulation field volume and/or centroid of stimulation) that substantially matches the corresponding field characteristic of the algorithmic model of baseline therapy field. Processor 60 may model any new therapy programs to determine whether the new therapy programs generate therapy fields that approximate one or more field characteristics of the baseline therapy field.

In another example, processor 60 may implement a tree-based technique for modifying a current therapy program. A therapeutic tree may include a plurality of levels that are associated with a different therapy parameter. The tree may include nodes that are connected to nodes of adjacent levels. A clinician or patient may interact with processor 60 via user interface 64 in order to create a program path by moving through one node at each level of the tree according to efficacy feedback from patient 12 and/or one or more sensors that detect physiological parameters of patient 12.

Examples of tree-based techniques for modifying a therapy program or generating a new therapy program are described in commonly-assigned U.S. patent application Ser. No. 11/799,114 to Gerber et al., entitled, "TREE-BASED ELECTRICAL STIMULATION PROGRAMMING FOR PAIN THERAPY," and filed on Apr. 30, 2007; commonly-assigned U.S. patent application Ser. No. 11/799,113 to Gerber et al., entitled, "TREE-BASED ELECTRICAL STIMULATOR PROGRAMMING," and filed on Apr. 30, 2007; and commonly-assigned U.S. patent application Ser. No. 11/414,527 to Gerber et al., entitled, "TREE-BASED ELECTRICAL STIMULATOR PROGRAMMING," and filed on Apr. 28, 2006.

As described in U.S. patent application Ser. No. 11/799,114 to Gerber et al., stimulation parameter types (e.g., electrode combination, voltage or current amplitude, pulse width, and frequency) may be arranged in a tree-like structure so that higher priority adjustments occur at higher levels of the tree and lower priority adjustments occur at lower levels of the tree. For example, the parameters may be prioritized so that parameters believed to have the largest impact on efficacy are placed in upper levels of the tree, while parameters having lesser impacts are placed in lower levels of the tree. In one example provided in U.S. patent application Ser. No. 11/799,114 to Gerber et al., one level of the tree may contain nodes that represent adjustments to pulse rate, while another level of the tree contains nodes that represent adjustments to pulse width, and yet another level contains nodes that represent adjustments in voltage or current amplitude. If a selected node of the tree produces a therapeutic efficacy improvement that exceeds a threshold level, then programming proceeds down the tree to the next level of nodes connected to the selected node. If the selected node does not produce an efficacy improvement above the threshold level, then programming proceeds to other nodes at the same level of the tree as the selected node. The threshold level may be a subjective pain level based upon normal pain perceived by the patient without therapy.

In one example of modifying a current therapy program with the aid of a therapeutic tree, processor 60 may move up one level on the therapeutic tree, and patient 12 may evaluate the nodes at this level, such that processor 60 may determine if any nodes provide better efficacy than the current therapy program. If no nodes at the selected level provide better efficacy, processor 60 may move up one more level on the therapeutic tree and evaluate a different therapy parameter. If at least one evaluated node provides better efficacy, processor may select the best efficacy node based upon patient 12 feedback. Processor 60 may then move down one level on the therapeutic tree from the selected node and select a node in the lower level based on patient feedback. After selecting the nodes that indicate the therapy parameter values that result in the best therapy for patient 12, processor 60 may set the stimulation parameter values defined by program path through the therapeutic tree as the modified therapy program and control IMD 14 to deliver therapy in accordance with the modified therapy program.

In another example, rather than selecting an alternative stored therapy program or generating a modified therapy program, processor 60 may modify a particular therapy parameter value of the current therapy program using rules stored within memory 62. The rules may indicate, for example, that a voltage or current amplitude should be increased if an impedance of one of the electrodes 35, 37 of the electrode combination of the current therapy program increases. The increased voltage or current amplitude may help compensate for a faulty electrode that delivers minimal or no electrical stimulation signals to patient 12.

In another example, processor 60 may implement a genetic algorithm-based technique for modifying a current therapy program (88), such as the one described in commonly-assigned U.S. Pat. No. 7,239,926 to Goetz et al., entitled, "SELECTION OF NEUROSTIMULATION PARAMETER CONFIGURATIONS USING GENETIC ALGORITHMS," which issued on Jul. 3, 2007. In one example described in U.S. Pat. No. 7,239,926 to Goetz et al., genetic algorithms provide guidance in the selection of stimulation parameter values by suggesting the parameter values that are most likely to be efficacious given the results of tests already performed during an evaluation session. Genetic algorithms encode potential solutions to a problem as members of a population of solutions. This population is then judged based on a fitness function. The best performers, i.e., the most fit solutions, are then retained and a new generation is created based upon their characteristics. The new generation is composed of solutions similar in nature to the best performers of the previous generation.

In accordance with U.S. Pat. No. 7,239,926 to Goetz et al., processor 60 may select a first electrode combination (i.e., the electrodes selected for therapy delivery and the polarities of the selected electrodes) for therapy delivery by IMD 14, receive an indication of observed efficacy of the first electrode configuration, and select a second electrode configuration for IMD 14 based on the indication of observed efficacy and a genetic algorithm. The genetic algorithm may suggest crossover between different solutions identified by the genetic algorithm or mutation of one or more solutions identified by the genetic algorithm, or random electrode changes.

After modifying the current therapy program (88), processor 60 may determine whether the modified therapy program is a suitable alternative by receiving feedback relating to the efficacy the modified therapy program. The feedback may be received from patient 12 via programmer 20 and/or sensors that sense one or more patient physiological parameters that are indicative of an efficacy of therapy. For example, in the case of electrical stimulation for urinary or fecal incontinence therapy, the sensors may indicate the number of involuntary voiding events, as described in U.S. patent application Ser. No. 11/414,527 to Gerber et al.

Alternatively, processor 60 may determine whether the modified therapy program is a suitable alternative by generating an algorithmic model of a modified therapy field resulting from the modified therapy program and comparing at least one field characteristic of the algorithmic model of the modified therapy field to the algorithmic model of the baseline therapy field. In order to generate the algorithmic model of the modified therapy field, processor 60 may implement an algorithm similar to that used by to generate the baseline algorithmic model.

FIG. 6 is a flow diagram of another example technique for modifying a therapy program based on information indicative of a change in a therapy field. IMD 14 delivers therapy to patient 12 according to the therapy parameter values of a current therapy program, and processor 60 stores an indication of the current therapy program within therapy programs section 76 of memory 62 or within another device (80). Processor 60 of programmer 20 receives information indicative of a change in a therapy field (82). As described with respect to FIG. 4, examples of information indicative of a change in a therapy field are information indicative of a change in the hardware of therapy system 30. The information indicative of the change in the therapy system hardware may include, for example, a change in impedance of one or more electrodes 35, 37 of leads 34, 36, a detected movement of one or both leads 34, 36 or a detected change in spacing between leads 34, 36, an increase in the total delivered energy per unit of time, or sensor feedback indicating, e.g., an increase in the number of patient events related to the patient condition.

In the technique shown in FIG. 6, information indicative of a change in a therapy field may additionally or alternatively include information relating to the efficacy of the therapy delivery according to the current therapy program. Efficacy information may include information indicating that patient 12 is experiencing increased symptoms of a patient condition for which the therapy system 10, 30 is used to manage or experiencing increased side effects from the therapy delivery. Increased symptoms or side effects may suggest that the therapy field has changed, and that a modification to one or more of the therapy parameter values defined by the current therapy program is desirable.

In some examples, the information relating to the efficacy of the therapy delivery may include feedback from patient 12, e.g., provided via programmer 20. For example, in one example, programmer 20 may include a dedicated button or another user input mechanism that patient 14 may press or otherwise interact with each time a particular patient event occurs, such as a seizure, a pain level above a particular threshold (which may be subjectively assessed by patient 12) or an incontinence event. The patient event may be selected to be a symptom of the patient condition for which the therapy system is used to treat or a side effect of the electrical stimulation therapy. Processor 60 may store an indication, such as a flag, value or signal, upon activation of the event button (or other input mechanism). Upon reaching a threshold number within a particular time frame (e.g., an hour, days, weeks or months), processor 60 may determine that the therapy field has changed due to the decreased therapeutic efficacy of the therapy system (e.g., suggested by an increase of symptoms or an increase in side effects). Thus, a certain number of event indications may provide information indicative of a change in a therapy field.

Instead of or in addition to patient input to provide information relating to the efficacy of the therapy delivery by the current therapy program, information from sensors may provide information suggesting a change in efficacy of the current therapy program. As discussed above, therapy systems 10, 30 may include one or more sensors 26 (FIG. 1A), which may monitor a patient parameter that changes in response to the efficacy of therapy, such as in response to an increase in patient symptoms or an increase in patient side effects. For example, if therapy system 10 delivers therapy to manage a seizure disorder of patient 12, sensor 26 may include an accelerometer, a bonded piezoelectric crystal, a mercury switch, or a gyro to monitor patient activity level to detect the occurrence of a seizure, e.g., by detecting the abnormal body movements. In yet another example, sensor 26 may monitor a heart rate of patient 12, and a change in heart rate may indicate an onset of a seizure.

Sensing electrodes on leads 16, 34, 36 may also be used to detect the occurrence of a seizure, e.g., based on EEG or ECoG signals or other bioelectrical brain signals. Processor 60 of programmer 20 may receive the signals from the sensing electrodes or sensor 26 and determine whether the signals indicate the occurrence of a seizure. For example, processor 60 may compare the EEG or ECoG waveform to a threshold amplitude value that indicates a seizure occurred, or processor 60 may perform a temporal correlation or frequency correlation with a template signal, or combinations thereof in order to determine whether a seizure has occurred. Alternatively, processor 40 of IMD 14 may determine whether a seizure occurred and transmit an indication, such as a flag, value or other marker, to programmer 20.

Processor 60 may record each seizure occurrence, and upon reaching a threshold number of seizures within a particular time frame (e.g., an hour, days, weeks or months) or a particular pattern of seizures, processor 60 may determine that the therapy field has changed due to the increase in the number of seizures experienced by patient 12. Thus, a certain number of seizure events may provide information indicative of a change in a therapy field.

In examples in which therapy system 10 provides DBS to manage a movement disorder of patient or a mood disorder of patient 12, the activity level of patient 12 may indicate the efficacy of therapy. For example, a decreased activity level may indicate that patient 12 is experiencing increased tremors or is in a depressive mood state, and, therefore, a therapy field that was determined to provide efficacious therapy to patient 12 may have changed. Accordingly, in some examples, sensor 26 may monitor various patient parameters that indicate a patient activity level, such as heart rate, respiration rate, respiratory volume, core temperature, blood pressure, blood oxygen saturation, partial pressure of oxygen within blood, partial pressure of oxygen within cerebrospinal fluid, muscular activity, arterial blood flow, EMG, EEG, ECoG, and ECG.

Processor 40 of IMD 14 or processor 60 of programmer 20 may determine activity counts for patient 12 while therapy is delivered to patient according to the current therapy program, and associate the activity counts with the current therapy program. Example systems, devices, and techniques for determining activity counts and associating activity counts with therapy programs are described in U.S. patent application Ser. No. 10/825,965 to Heruth et al., which is entitled, "COLLECTING ACTIVITY INFORMATION TO EVALUATE THERAPY," and was filed on Apr. 15, 2004. As described in U.S. patent application Ser. No. 10/825,965 to Heruth et al., processor 40 of IMD 14 or processor 60 of programmer 20 may determine a number of activity counts based on signals generated by sensor 26, and the number of activity counts may be stored as an activity level associated with the current therapy program. For example, the number of activity counts may be a number of threshold crossings by a signal generated by sensor 26, such as an accelerometer or piezoelectric crystal, during a sample period, or a number of switch contacts indicated by the signal generated by sensor 26, such a mercury switch during a sample period. Upon determining that the activity level (or the number of activity counts) falls below a particular threshold level for a certain time range, such as one or more hours, days or weeks, processor 40 or 60 may determine that the current therapy field has changed, and, therefore, it is desirable to modify the current therapy program. Thus, the activity level associated with the current therapy program may provide information indicative of a change in a therapy field.

In examples in which therapy system 10 provides DBS to manage a mood disorder, such as bipolar disorder or major depressive disorder, of patient 12, or therapy system 30 provides SCS to manage the patient's pain, the sleep quality of patient 12 may indicate the efficacy of therapy. The quality of the patient's sleep may be determined using any suitable technique. In one example, processor 40 of IMD 14 determines values of one or more sleep metrics that indicate a probability of a patient being asleep based on the current value of one or more physiological parameters of the patient, as described in U.S. patent application Ser. No. 10/825,964 to Heruth et al., which is entitled, "DETECTING SLEEP" and was filed on Apr. 15, 2004. Processor 40 may then determine the number of disruptions in the patient's sleep, e.g., based on the number of times processor 40 determines patient 12 is not asleep during a particular time frame (e.g., 10 p.m. to about 8 a.m.).

As described in U.S. patent application Ser. No. 10/825,964 to Heruth et al., sensor 26 may generate a signal as a function of at least one physiological parameter of a patient that may discernibly change when the patient is asleep. Example physiological parameters include activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. In some examples, the processor determines a value of a sleep metric that indicates a probability of the patient being asleep based on a physiological parameter. In particular, the processor may apply a function or look-up table to the current value and/or variability of the physiological parameter to determine the sleep metric value. The processor may compare the sleep metric value to a threshold value to determine whether the patient is asleep.

In some examples, a therapy system may be configured to deliver electrical stimulation therapy to patient 12 in order to manage urinary or fecal incontinence. In such cases, sensor 26 may be positioned to detect the occurrence of an involuntary urinary or fecal voiding event. Sensor 26 may provide the signals to programmer 20, and processor 60 may evaluate the efficacy of the current therapy program based on the number of involuntary voiding events associated with the current therapy program. Sensor 26 may, for example, detect a voiding event by detecting nerve impulses of a sacral or pudendal nerve, as described in U.S. patent application Ser. No. 11/414, 504 to Rondoni et al., which was filed on Apr. 28, 2006 and is entitled, "VOIDING DETECTION WITH LEARNING MODE."

As other non-limiting examples, sensor 26 may be disposed adjacent to patient 12 via an undergarment worn by patient 12, and may be configured to detect the presence of fluid, which may indicate that an involuntary voiding event has occurred. For example, as described in U.S. patent application Ser. No. 11/414,626 to Rondoni et al., which was filed on Apr. 28, 2006 and is entitled, "EXTERNAL VOIDING SENSOR SYSTEM," sensor 26 may determine wetness by detecting a decrease in resistance between two electrodes of the sensor, or by detecting fluid pH, impedance, electrolyte concentration, or other characteristics of the fluid to identify that the fluid is urine.

Processor 60 may compare the total number of involuntary voiding events that occurred during therapy delivery via the current therapy program with a threshold value, which may be stored in memory 62. In other examples, processor 60 may compare the average number of voiding events for a sample period of time (e.g., average number of voiding events per day or week) with a threshold value. Upon crossing the threshold, processor 60 may determine that the current therapy program is no longer effective, and that the therapy field may have changed.

As other examples, in order to indicate the efficacy of the current therapy program in managing urinary incontinence, sensor 26 may be configured to provide information relating to the function of the bladder of patient 12, or any other segment of the patient's urinary tract, in storing releasing and passing urine. For example, as described in U.S. patent application Ser. No. 11/263,170 to Gerber, which was filed on Oct. 31, 2005 and is entitled, "IMPLANTABLE MEDICAL DEVICE PROVIDING ADAPTIVE NEUROSTIMULATION THERAPY FOR INCONTINENCE," sensor 26 may monitor patient parameters such as bladder pressure, bladder contractile force, urinary sphincter pressure, urine flow rate, urine flow pressure, voiding amount, and the like. These urodynamic parameters of patient 12 may indicate a decrease in efficacy of the current therapy program. The urodynamic parameters may, but do not necessarily indicate the occurrence of an involuntary voiding event.

In other examples, sensor 26 or other sensing devices may provide any suitable information indicative of a change in therapeutic efficacy that may indicate a change in therapeutic efficacy, which may suggest there has been a change in the therapy field. The patient parameters that sensor 26 monitors may differ depending upon the patient condition for which the therapy program is implemented to manage.

After receiving information indicative of the change in the therapy field, processor 60 may modify the current therapy program based on the information by selecting an alternative therapy program or changing at least one parameter value of the current therapy program (90). For example, if the information indicates an increase in impedance of at least one of electrodes 35, 37 that is activated in the electrode combination of the current therapy program, processor 60 may increase a voltage or current amplitude of the therapy program in order to compensate for any decreased stimulation delivered by the electrode with the increased impedance. As another example, if the information indicates that the patient's activity level has decreased, processor 60 may select therapy program from a list that is ordered according to activity levels. As described in U.S. patent application Ser. No. 10/825,965 to Heruth et al., activity levels may be determined for each of a plurality of stored therapy programs. The therapy programs may then be ordered according to activity metric values associated with each therapy program, where the metric value is determined based on the activity levels associated with the therapy program. Accordingly, upon determining that the patient's activity level has decreased, processor 60 may select a therapy program that is associated with a higher activity level or otherwise modify the current therapy program. Other therapy program modifications are contemplated, such any of the other techniques described above with respect to FIG. 4.

Processor 60 may receive feedback relating to the efficacy of one or more modifications to the current therapy program in order to determine whether the modified therapy program provides efficacious therapy to patient 12. The feedback may be received from patient 12 and/or sensors, such as sensor 26 or other sensors, that sense one or more patient physiological parameters that are indicative of an efficacy of therapy. For example, in the case of electrical stimulation for urinary or fecal incontinence therapy, the sensors may indicate the number of involuntary voiding events, as described in U.S. patent application Ser. No. 11/414,527 to Gerber et al. The feedback relating to the efficacy of one or more modifications to the current therapy program may be used in a closed-loop or a modified open-loop system to automatically adjust the therapy parameter values of the current therapy program to achieve an efficacious therapy program.

After modifying the current therapy program (90), processor 60 generates an algorithmic model of a modified therapy field resulting from therapy delivery according to the parameter values of the modified therapy program (92). The algorithmic model of the modified therapy field may be generated using the same or a different algorithm used to generate the algorithmic model of the baseline therapy field, where the algorithm(s) may be stored within algorithms section 78 of memory 62. For example, the algorithmic model of the modified therapy field associated with the modified therapy program may be based on an anatomy of patient 12, the therapy program determined to provide efficacious therapy to patient 12, and the hardware characteristics of therapy system 30.

Processor 60 then compares at least one characteristic of the algorithmic model of the modified therapy field model to a respective characteristic of the algorithmic model of the baseline therapy field model (94). As described above with respect to FIG. 4, the characteristics of the therapy fields may include, but are not limited to, centroids of stimulation, the total volumes or cross-sectional areas, of the electrical field or activation field or the regions of the patient anatomy recruited by the therapy field.

If the one or more characteristics of the modified therapy field model are substantially similar to respective characteristics of the algorithmic model of the baseline therapy field, e.g., are within an acceptable range of the algorithmic model of the baseline therapy field, processor 60 may control IMD 14 to deliver therapy according to the modified therapy program (96). Processor 60 may, for example, transmit the therapy parameter values of the modified therapy program to IMD 14 or may transmit an indication of the therapy program, and processor 40 of IMD 14 may determine the therapy parameter values associated with the indicator, which may be stored within programs 52 of memory 42 of IMD 14.

On the other hand, if the comparison between the current and baseline therapy field models indicates that the one or more characteristics of the modified therapy field are not substantially the same as the characteristics of the baseline therapy field model, processor 60 may continue modifying the therapy program (90) until the one or more characteristics of a modified therapy program substantially match the characteristics of the baseline therapy field model, e.g., are within an acceptable range of the respective characteristics of the baseline therapy field model. The acceptable range may be determined by a clinician, and may be the range in which therapy delivery according to the selected therapy program (i.e., the current or modified therapy program) provide efficacious therapy to patient 12. In some examples, an acceptable range includes an absolute range of values or a percent change from a mean, median or another predetermined value.

As previously described, in some examples, programmer 20 or another computing device may include a user interface that enables a clinician to program IMD 14 by defining one or more stimulation fields and subsequently generating the therapy programs that may achieve the defined stimulation fields, as described in U.S. patent application Ser. No. 11/591,299 to Stone et al., entitled, "ELECTRICAL AND ACTIVATION FIELD MODELS FOR CONFIGURING STIMULATION THERAPY" and U.S. patent application Ser. No. 11/591,188 to Goetz et al. and entitled, "PROGRAMMING INTERFACE WITH A CROSS-SECTIONAL VIEW OF A STIMULATION LEAD WITH COMPLEX ELECTRODE ARRAY GEOMETRY."

The techniques described in U.S. patent application Ser. Nos. 11/591,299 to Stone et al. and 11/591,188 to Goetz et al. may also be used to generate an algorithmic model of a baseline therapy field. For example, after programming IMD 14 with a therapy program that provides efficacious therapy to patient 12, a user may generate an electrical field model that estimates where the electrical current will propagate from the electrodes 35, 37 of implanted leads 34, 36 within brain 18 or an activation field model that estimates which neurons within the electrical field model will be activated by the voltage of the electrical field during therapy. In general, the electrical field model or the activation field model may estimate the anatomical structures that will be affected by a therapy program. Thus, the electrical field model or the activation field model may be stored as an algorithmic model of a baseline therapy field, which represents a therapy field that provides efficacious therapy to patient 12.

Figure 7:
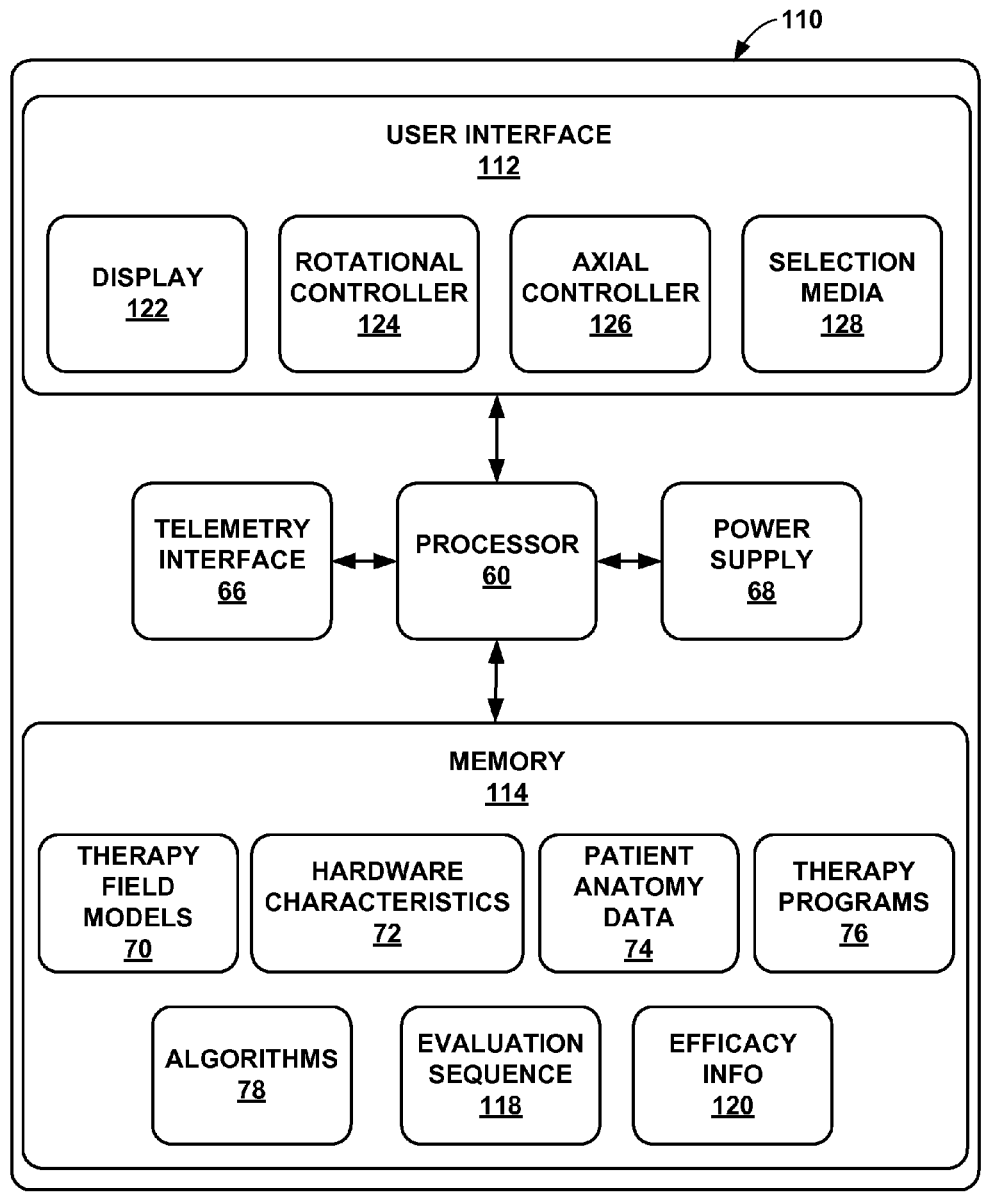
FIG. 7 is a block diagram illustrating an example programming device that may enable a clinician to define an algorithmic model of a baseline therapy field.

FIG. 7 is a block diagram illustrating an example programming device 110 that presents a user interface to a clinician that enables the clinician to define an algorithmic model of a baseline therapy field. The programming device 110 shown in FIG. 7 may be an example of the programmer 20 of FIG. 1. An algorithmic model of the baseline therapy field may be defined by a clinician to target a particular anatomical structure or target tissue of a particular patient or may be defined to target a particular anatomical structure or target tissue for more than one patient, e.g., as a general therapy field that indicates a therapy field that may provide efficacious therapy for a particular patient condition. The programming device 110 shown in FIG. 7 is described in further detail in U.S. patent application Ser. No. 11/591,188 to Goetz et al.

While the remainder of the description of FIGS. 7-17 primarily refers to therapy system 10 of FIG. 1A including a single lead 16, in other examples, the techniques for selecting therapy programs and generating an algorithmic model of a baseline therapy field may be applied to a therapy system including more than one lead, as well as a therapy system implanted proximate to other target tissue sites, such as therapy system 30 of FIG. 1B that provides spinal cord stimulation to patient 12.

Programming device 110 includes processor 60, telemetry interface 66, and power supply 68, which are described above with respect to FIG. 3. In addition, programming device 110 includes a user interface 112 and memory 114. Memory 114 may include any volatile, non-volatile, magnetic, optical, or electrical media, such as a RAM, ROM, NVRAM, EEPROM, flash memory or any other digital media. Memory 114 stores programs 76 specifying electrode combinations, electrode polarities, and stimulation parameter values that may be transmitted to IMD 14. In addition to programs 76, memory 114 may store therapy field models 70, hardware characteristics 72 of therapy system 30, patient anatomy data 74, and algorithms 78 for generating algorithmic models of therapy fields. In addition, memory 114 may store an evaluation sequence 118 that guides the user in the selection of electrode combinations and stimulation parameter values, or automatically selects electrode combinations and stimulation parameter values for evaluation of efficacy. For example, evaluation sequence 118 may specify a predetermined progression of electrode combinations to be selected for evaluation, or provide rules for dynamic selection of electrode combinations during the course of evaluation.

Memory 114 also may record efficacy information 120 associated with one or more of the stored programs 76. Specifically, upon selection of an electrode combination and other stimulation parameter values as a program, programming device 110 may direct IMD 14 to apply the program. Upon application of the program, the patient may provide feedback concerning efficacy. The user, which may be a clinician or the patient 12, then records the efficacy information in memory 114 of programming device 112. In this manner, different programs may be rated in terms of efficacy so that the user ultimately may select an effective electrode combination and other stimulation parameter values.

A user interacts with processor 60 via user interface 112 in order to identify efficacious electrode combinations and other stimulation parameter values as described herein. Processor 60 may provide display 100, i.e., a graphical user interface (GUI), via user interface 112 to facilitate interaction with the user. User interface 112 may also include one or more input media, such as lights, audible alerts, or tactile or other somatosensory alerts.

In the example shown in FIG. 7, the input media of user interface 112 includes rotational controller 124 and axial controller 126. Rotational controller 124 permits the user to move electrode combinations or stimulation fields around a representation of lead 16 presented on display 122 by selecting combinations of electrodes at different angular positions. Axial controller 126 permits a user to move electrode combinations or stimulation fields up or down along the length of lead 16 within the 2D or 3D modeling environment presented on display 122 by selecting different combinations of electrodes. In addition, axial controller 126 and rotational controller 124 may be configured to permit the user to view different electrodes, e.g., from multiple perspectives. User interface 112 also may present selection media 128 to permit the user to select particular electrode combinations for activation.

Using evaluation sequence 118, processor 60 may run a user-controlled test of a predetermined or dynamically generated sequence of electrode combinations to identify effective electrode combinations for alleviating symptom areas. Processor 60 may receive a pre-defined set of electrode combinations to test from a clinician and store the pre-defined set of electrode combinations as a set of programs, either alone or in combination with stimulation parameter values. Alternatively, processor 60 may execute an electrode combination search algorithm according to evaluation sequence stored 118 in memory 114 to select individual electrodes or electrode combinations to test.

Processor 60 controls IMD 14 via telemetry interface 66 to test selected electrode combinations by controlling the stimulator to deliver electrical stimulation therapy to patient 12 via the selected electrode combinations. In particular, processor 60 transmits programming signals to IMD 14 via telemetry interface 66. As a sequence of electrode combinations proceeds, the programming signals may be transmitted at a rate consistent with the control input provided by a user. In this manner, the user may quickly observe the effects of each increment in the change between electrode combinations. In some cases, e.g., for DBS applications, effects of an electrode or parameter change may not be immediately evident. In such cases, a change may be activated and evaluated over a period of minutes, hours, or days before another change is initiated.

After completion of electrode testing, processor 60 may transmit one or more of the programs created by the clinician to IMD 14 via telemetry interface 66 for storage in IMD 14, or to another programmer used by patient 12 to control delivery of electrical stimulation therapy, e.g., via wireless or wired input/output interface. In either case, the selected electrode combinations can then be used to deliver therapy chronically or over an extended period of time.

Programming device 110 may be provided in the form of a handheld device, portable computer, or workstation that provides a user interface to a clinician or patient. The clinician or patient interacts with user interface 112 to program stimulation parameter values for IMD 14 via external programming device 110. Hence, various aspects of user interface 112 described herein may be provided in the form of clinician programmer, a patient programmer or both.

During a programming session, a clinician may select the stimulation parameter values of a therapy program that define the therapy delivered to patient 12 by IMD 14 with the aid of the programming device 110 shown in FIG. 7. The clinician interacts with the user interface 112 to manually select and program particular electrodes of lead 16 via an electrode selection view, or select an electrode level of the lead and adjust a stimulation field resulting from a particular electrode selection. Once the clinician has defined the one or more stimulation fields, the programming device 110 generates the stimulation parameter values associated with each of the stimulation fields. The stimulation parameter values may be transmitted to IMD 14 or stored within programs 76 section of the programmer's memory 114. Hence, user interface 112 of the programming device 110 may permit a user to manually select electrode combinations and associated stimulation parameter values, or simply specify and manipulate a stimulation field in terms of size, direction and shape, in which case the programming device 110 or IMD 14 may automatically adjust electrode combinations and parameter values to approximate the desired stimulation field. In some examples, the user interface may restrict the ability of the user to define the stimulation fields based upon the stimulation capabilities of IMD 14 and lead 16. For example, the clinician may not make the stimulation field larger when the voltage or current amplitude cannot be increased any further, or when no more electrodes are available in the desired direction of the stimulation field.

Additionally, the user interface may restrict the user from applying the stimulation field to anatomical regions specifically banned from stimulation. These anatomical regions may severely alter the physiology of patient 12 and cause detrimental side effects or irreversible side effects. Accordingly, the user may manually lockout potentially unsafe electrodes or electrode levels based upon the actual implantation location of lead 16 within brain 18 or another target tissue site. Therefore, the user interface may be configured to prevent the user from selecting particular electrodes during the programming of stimulation parameter values. Alternatively, or additionally, some electrodes or electrode levels may have predetermined parameter ranges that cannot be violated. For example, a minimum field value or parameter value may be specified to maintain field strength at a minimum level. Similarly, a maximum field value or parameter value may be specified to prevent stimulation in excess of a given level.

The stimulation field selected by a clinician during the programming of IMD 14 may be stored within therapy field models 70 section of memory 114 as an algorithmic model of a baseline therapy field. That is, user interface 112 may present a representation of one or more implanted leads and a representation of the patient anatomy proximate the implanted lead. The clinician may define a desired stimulation field over the representation of the patient anatomy, relative to the representation of the one or more implanted leads or relative to both the representation of the patient anatomy and the implanted leads. The clinician-defined stimulation field may be the algorithmic model of the baseline therapy field that provides efficacious therapy to patient 12.

As previously indicated, processor 60 may generate a therapy program that may achieve the clinician-defined stimulation field. After implementation of the therapy program, processor 60 may receive an indication that the therapy field has changed due to a change in the hardware characteristics of therapy system 10. As described with respect to FIGS. 4 and 6, the changed therapy field or a therapy field of a modified therapy program may be compared to the baseline therapy field, i.e., the clinician-defined stimulation field, in order to determine whether the modification to a therapy program is necessary and/or acceptable for maintaining efficacious therapy.

Figure 8:
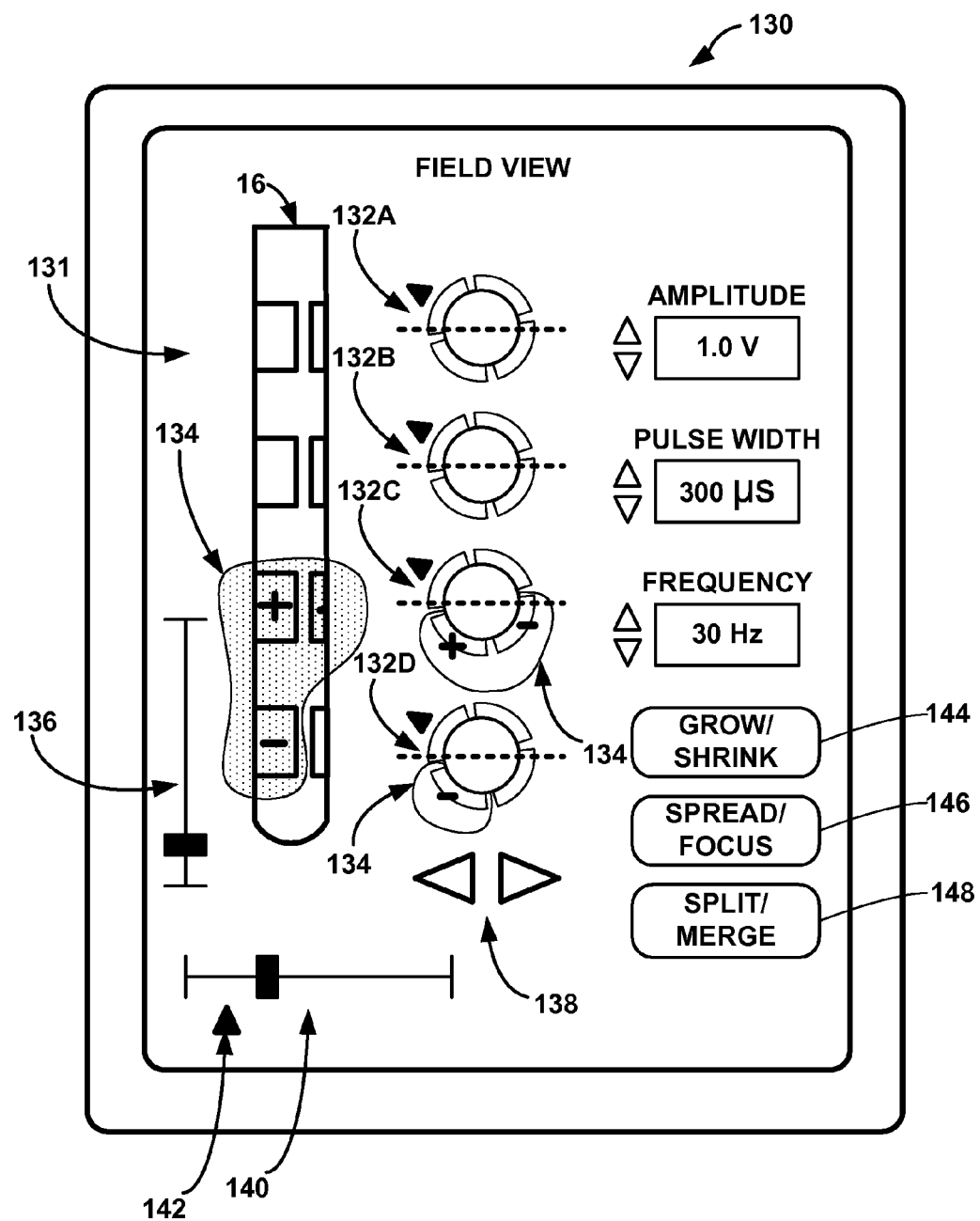
FIGS. 8-10 illustrate example graphic user interfaces (GUIs) that may be presented on a display of a programming device in order to aid the generation of efficacious therapy programs and algorithmic models of baseline therapy fields.

FIG. 8 illustrates a schematic representation of an example graphic user interface (GUI) 130 that may be presented on a display 122 of programming device 110 of FIG. 7. By interacting with GUI 130, a user may generate an algorithmic model of an electrical stimulation field produced by a selected electrode combination. For example, the user may change the size, shape or position of the field using graphical input media such as cursor or stylus control. In some examples, the user may be able to create a stimulation field in the field view and direct processor 60 of programming device 110 to generate stimulation parameter values that would best match the stimulation field. The generated electrical stimulation field may be stored as an algorithmic model of a baseline therapy field.

GUI 130 illustrates lead 16, which includes a complex electrode array geometry. A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a lead. This type of electrode array geometry is shown in FIG. 2. Another example of a simple electrode array geometry is a planar array of electrodes on a paddle lead.

In the example of FIG. 8, rather than including four electrodes 17 as shown in FIG. 1A, lead 16 includes four electrode "levels" at different axial positions along the length of the lead. Each level includes four electrodes generally arranged in a ring. However, the electrodes are non-contiguous with one another. The electrodes may be referred to as segmented electrodes or electrode segments. Each electrode is coupled to a respective electrical conductor within lead 16. Hence, lead 16 includes multiple electrical conductors, e.g., wires, cables or the like, that extend from the proximal end of the lead to respective electrodes to electrically couple the electrodes to electrical terminals associated with IMD 14.

Each electrode is positioned at a different angular position around the circumference of implantable lead 16, which has a generally circular cross-section in the example of FIG. 8. Each electrode is independently selectable so that stimulation energy can be delivered from the lead at different axial and angular positions. In some examples, lead 16 may include combinations of complex electrode array geometries and simple electrode array geometries. For example, ring electrodes that extend about the entire circumference of the lead may be used in combination with electrodes disposed at different axial and angular positions. Selective activation of the electrodes carried by lead 16 can produce customizable stimulation fields that may be directed to a particular side of lead 16 in order to isolate the stimulation field around a target anatomical region of brain 18.

GUI 130 illustrates a side view 131 and multiple cross-sectional views 132A-132D of lead 16 in alignment with corresponding electrode levels. In the example of FIG. 8, the user has selected an initial electrode combination, either manually or by selection for a set of electrode combinations provided by programming device 110, and the selected electrode combination is illustrated in GUI 130. GUI 130 presents a representation of a stimulation field 134 defined by the user and produced by the selected electrode combination, given stimulation parameter values selected by the user and general tissue characteristics stored within programming device 110.

The size and shape of stimulation field 134 may be established based on generic physical characteristics of human tissue and known physical characteristics of the electrodes of lead 16. In other words, stimulation field 134 displayed in field view 175 of GUI 130 may only be an approximation of what the stimulation field would be in brain 18 of a specific patient 12. However, in some examples, physical characteristics of the actual anatomical structure of patient 12 being treated may be used to generate stimulation field 134. This anatomical structure information may be presented to programmer 110 in the form of patient anatomical data generated by an imaging modality, such as computed tomography (CT), magnetic resonance imaging (MRI), or any other volumetric imaging system and stored within patient anatomy data section 74 of memory 114 (FIG. 7). In the example that uses the patient anatomical data, stimulation field 134 may be similar to an electrical field model, which is discussed in detail with reference to FIGS. 9 and 11. For example, stimulation field 134 may rely on tissue impedance models, field propagation models, and the like. In some examples, stimulation field 134 may be a representation of an electrical field, current density, voltage gradient, or neuron activation, applied to a generic human tissue or the anatomy of patient 12. In addition, the clinician may be able to switch between any of these representations when desired.

The user may move stimulation field 134 up or down relative to a longitudinal axis of lead 16 using vertical scroll bar 136 or some similar control interface. As stimulation field 134 moves up or down in response to the user input, programming device 110 automatically selects appropriate electrode combinations to support the vertical movement of stimulation field 134. For example, processor 60 may phase electrodes in and out as stimulation field 134 travels upward or downward, reducing the stimulation energy delivered from some electrodes as the stimulation field moves away from them, and increasing the stimulation energy delivered by other electrodes as the field moves toward them. Also, GUI 130 includes arrows 138 or similar input media that permit the user to transition between different electrode levels of the lead in cross-sectional views 132A-132D.

In addition, the user may rotate stimulation field 134 using horizontal scroll bar 140 or some similar control device. An arrow 142 may be provided next to horizontal scroll bar 140 to indicate the orientation of lead 16 relative to an anatomical structure. In addition, arrows may be provided in respective cross-section views 132A-D to maintain orientation. As the user rotates stimulation field 134, processor 60 of programmer 110 may automatically select appropriate electrode combinations to support the rotational movement of the stimulation field 134. As in the case of vertical movement, rotational movement of stimulation field 134 may be accomplished by gradually reducing the stimulation energy delivered to some electrodes as the stimulation field rotates away from them, and gradually increasing the stimulation energy delivered to other electrodes as the stimulation field rotates toward them. Side view 131 and cross-sectional views 132A-D permit the user to observe movement of stimulation field 134 from both an axial perspective and a rotational perspective.

Movement of stimulation field 134 using scroll bars 136, 140 or similar input media permits the user to evaluate different stimulation field positions without the need to manually select electrodes and manually enter parameter values. Instead, processor 60 of programming device 110 automatically selects electrodes and parameter values in response to movement of stimulation field 134 by the user. Although scroll bars 136, 140 are illustrated as examples of input media for movement of stimulation field 134, other types of input media may be used. Examples include up/down arrows or side-to-side arrows, which may be presented on a touch screen or formed by buttons or keys on programming device 110.

As a further alternative to manipulating the stimulation field 134, the user may select stimulation field 134 with a stylus, mouse, or other pointing device and drag the field upward, downward, or rotationally. In some examples, a mouse or other pointing device may support left or right click functionality to perform different operations relative to stimulation field 134. With a stylus, a first click on stimulation field 134 may initiate movement, dragging with the stylus directs movement relative to the schematic illustration of lead 16 in GUI 130, and a second click may terminate movement. In each case, processor 60 of programming device 110 responds to the specified movement by automatically adjusting the electrode combination and other stimulation parameter values to approximate the characteristics of stimulation field 134 presented by GUI 130 on display 122. As the stimulation parameter values change, the size and shape of stimulation field 134 presented on the display change. Similarly, as the electrode combination changes in terms of polarity or electrode selection, the size, shape or direction of stimulation field 134 presented on the display changes.

In other examples, processor 60 of programming device 110 may utilize stimulation templates and select the best fitting stimulation template set to a newly modified stimulation field 134. A stimulation template is a predetermined volumetric stimulation field that processor 60 of programming device 110 may substantially match to a desired stimulation field 134 from the clinician. An algorithm for generating a therapy field model that utilizes one or more stimulation templates to generate stimulation parameter values that fit the user defined stimulation field may be less computationally intensive for processor 60 compared to an algorithm that references multiple equations or lookup tables to generate the stimulation parameter values. The stimulation template may be a representation of an electrical field or other electrical stimulation related characteristic, e.g., current density, voltage gradient, or neuron activation, applied to a generic human tissue. For stored stimulation templates, processor 60 may adjust the current amplitude or voltage amplitude to alter the size of the stimulation template to cover the desired stimulation field 134 from the user. Examples of stimulation templates are described in U.S. patent application Ser. No. 11/591,188 to Goetz et al.

Processor 60 of programming device 110 may limit the rate of movement of stimulation field 134 within GUI 130. In other words, stimulation field 134 may only be moved a certain number of steps per second within GUI 130, or any other user interface that allows the clinician to drag the stimulation field. This rate movement limit may prevent unnecessary calculations or ensure patient comfort in real-time programming examples.

In addition to moving stimulation field 134, GUI 130 may permit the user to perform one or more operations that result in reconfiguration of the stimulation field. For example, the user may click on a border, i.e., an outer perimeter, of stimulation field 134, and drag it inward or outward to resize the stimulation field. Resizing by enlarging or shrinking stimulation field 134 in GUI 130 results in an increase or decrease in amplitude, pulse width or pulse rate of the stimulation energy. In some examples, enlarging or shrinking stimulation field 134 also may result in selection or de-selection of electrodes included in the existing electrode combination. In either case, processor 60 of programming device 110 adjusts the electrode combination and/or parameter values in response to the enlargement or shrinkage of stimulation field 134 by the user.

When a user clicks on stimulation field 134 border and drags it, the entire stimulation field may be expanded in two dimensions in equal proportions. Alternatively, stimulation field 134 may expand only in the direction in which the user drags the stimulation field. For example, horizontal dragging of the field perimeter to enlarge stimulation field 134 may result in overall enlargement of the cross-sectional seize of stimulation field 134, keeping the vertical to horizontal aspect ratio constant. Alternatively, horizontal dragging may result only in horizontal expansion, leaving the vertical dimension constant. The application of a constant or varying aspect ratio may be specified by a user as a user preference. Alternatively, programming device 110 may provide different aspect ratio modes on a selective basis for expansion and shrinkage of stimulation field 134.

To enlarge or shrink stimulation field 134, the user may simply click on the stimulation field border within GUI 130. Alternatively, the user may click on a grow/shrink button 144 as shown in FIG. 8, and then click on the border of stimulation field 134 to drag it inward or outward and thereby adjust the size of the stimulation field. In response, processor 60 of programming device 110 may automatically reconfigure the electrode combination and/or stimulation parameter values to approximate the resized stimulation field. In this way, a user may generate an algorithmic model of a baseline therapy field by directly manipulating the stimulation field 134. Other field adjustment functions such as spread/focus button 146 and split/merge button 148 may be provided by GUI 130. In each case, the user changes stimulation field 134 by simply changing the representation of the stimulation field 134 presented on GUI 130, thereby avoiding the need to manually select electrodes and parameter values. The operation of the buttons 144, 146, and 148 is described in further detail in U.S. patent application Ser. No. 11/591,188 to Goetz et al.

After selecting a desirable stimulation field 134, processor 60 of programming device 110 may generate algorithmic models of an electrical field and an algorithmic model of an activation field. The model of the electrical field or the model of the activation field may be stored as the algorithmic model of a baseline stimulation field.

Figure 9:
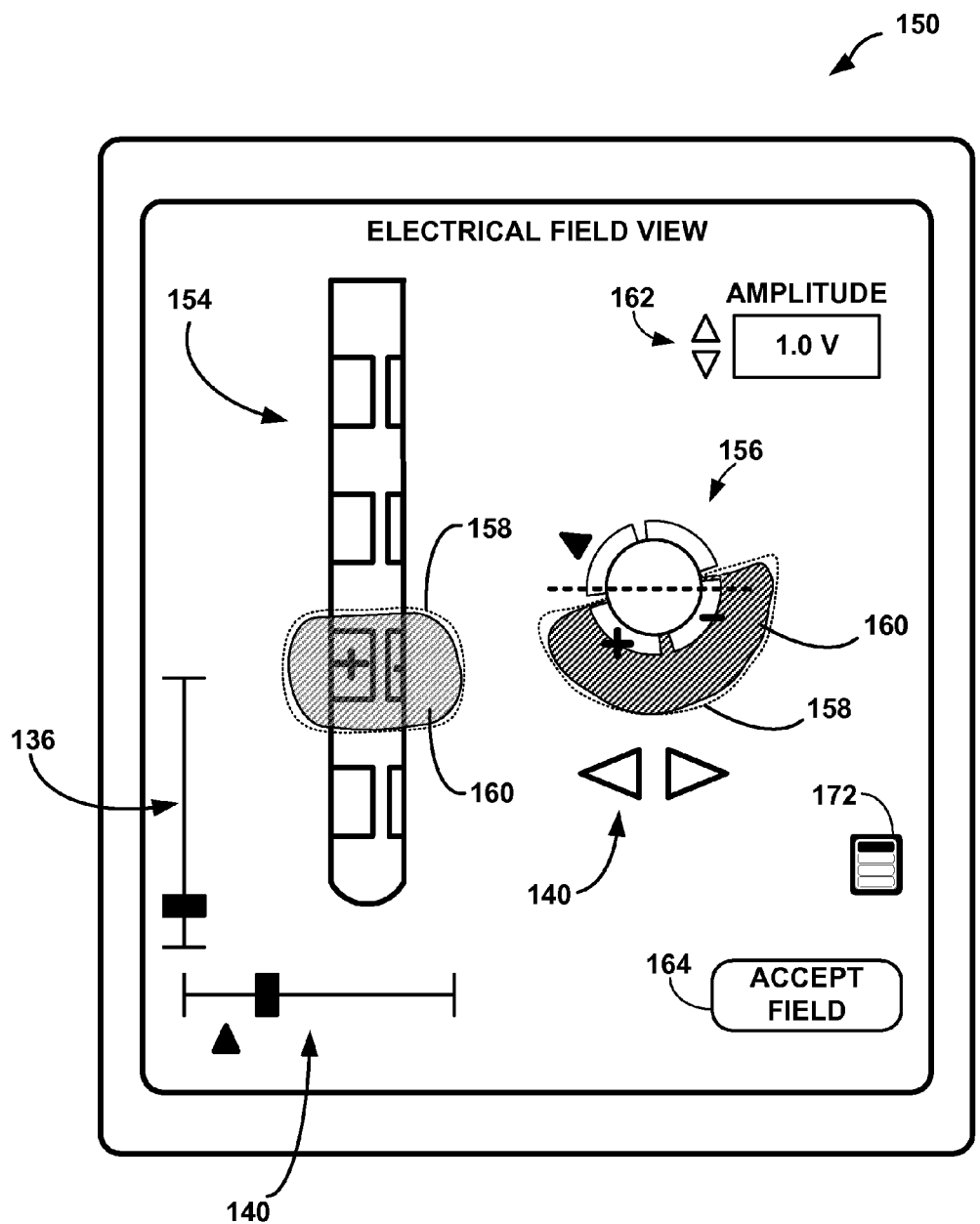
Figure 10:
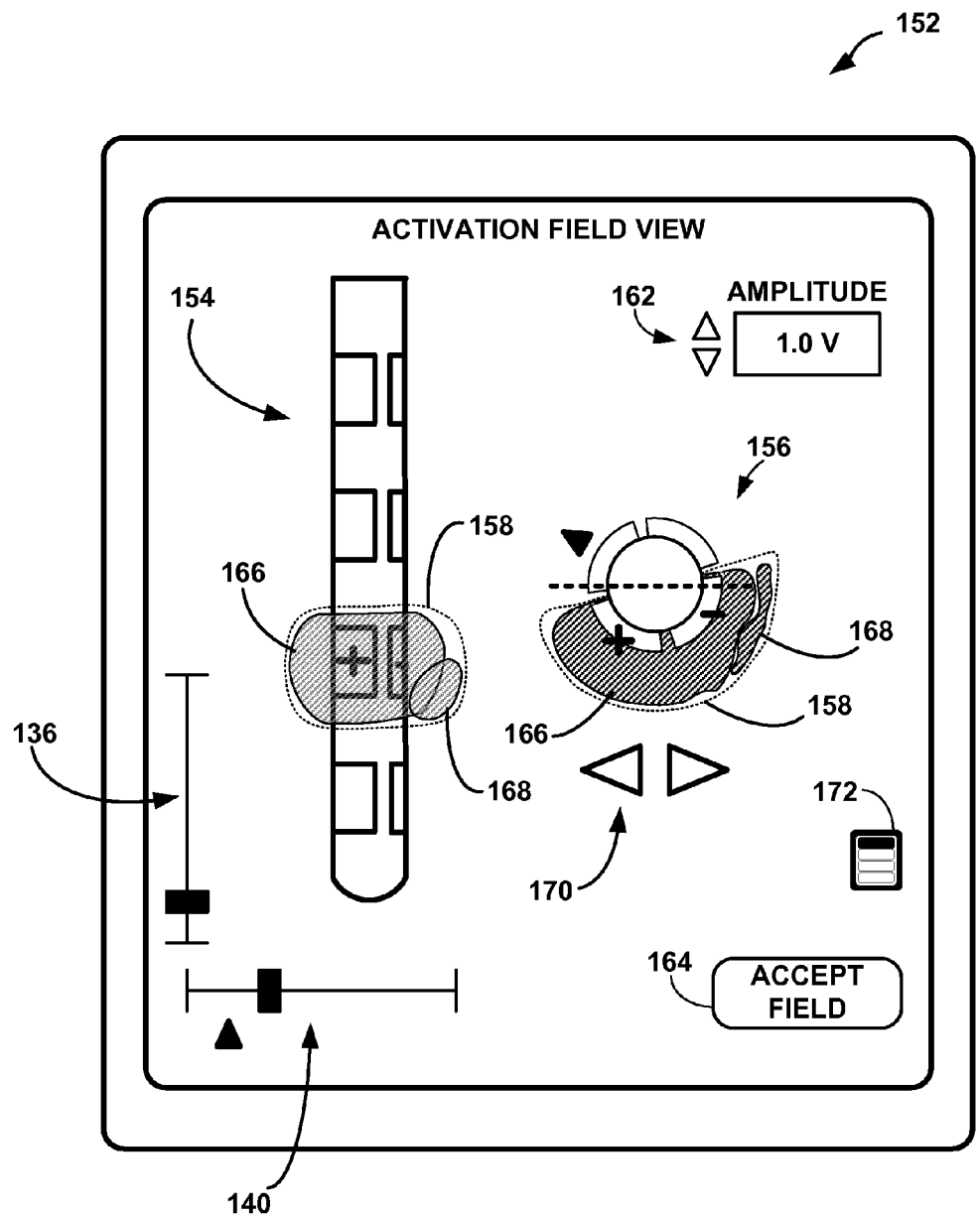

FIGS. 9 and 10 are schematic diagrams illustrating example GUIs 150, 152 that present electrical field models and activation field models, respectively, to a user. FIG. 9 illustrates an example GUI 150 that displays a stimulation field view to the user via display 122 of programming device 110. GUI 150 displays side view 154 and cross-sectional view 156 of implanted lead 16, and the user defines stimulation field 158 on the side and cross-sectional views, e.g., using the techniques described above with respect to FIGS. 7 and 8. Processor 60 of programming device 110 may generate stimulation parameter values for therapy based on the selected stimulation field 158 and generate an electrical field model 160, which estimates an electrical field that results from therapy delivery according to the stimulation parameter values associated with the selected stimulation field 158. In GUI 150, electrical field model 160 is displayed as an electrical field within the outer boundaries of stimulation field 158. In other examples electrical field model 160 may be a representation of another electrical stimulation related characteristic, e.g., current density, or voltage gradient. In addition, the clinician may be able to switch between any of these representations when desired.

Electrical field model 160 represents where the electrical current will propagate from the implanted lead 16 within tissue, as tissue variation within patient 12 may change the electrical current propagation from the lead in some directions. The variations in electrical field propagation may affect the ability of the therapy to actually treat a desired structure of brain 18 in examples in which IMD 14 delivers stimulation to brain 18 (FIG. 1A) or cause a side effect. The horizontal and axial views of electrical field model 160 illustrated in FIG. 9 are 2D slices of a volumetric electrical field model generated by processor 60 of programming device 110. Processor 60 utilizes an algorithm to generate electrical field model 160. In one example, the algorithm takes the patient anatomy data with electrical field model equations that define electrical current propagation into consideration. Accordingly, if the algorithmic model of the baseline therapy field includes electrical field 160, processor 60 may implement an algorithm that applies electrical field model equations that define how the electrical field propagates away from an origin location. The electrical field model equations may be specific to patient 12. The electrical field equations require the physical tissue characteristics of the tissue adjacent lead 16, which is included in the patient anatomy data set. From this information, processor 60 is able to generate the estimated electrical field 160 that will be produced in therapy.

Electrical field model 160 may differ from the selected stimulation field 158 because processor 60 generates stimulation field 158 using an algorithm that only considers general tissue characteristics, which are not specific to patient 12. In other examples, the electrical field equations may utilize matrices or other mathematical model of the electrical field. In this manner, electrical field 160 can be estimated and modeled for the user. Accordingly, the user may be able to increase or decrease the amplitude of the stimulation parameter values with an amplitude interface 162 in order to change the size and possibly shape of electrical field 160 or directly manipulate electrical field 160. If the user is satisfied with electrical field 160, the user may select accept field button 164 to transmit the stimulation parameter values to IMD 14. If desired, the electrical field 160 or the stimulation field 158 may be stored as an algorithmic model of a baseline therapy field. For example, upon activation of accept field button 164, processor 60 may automatically store electrical field 160 or stimulation field 158 within therapy field models section 70 of memory 114 (FIG. 7).

FIG. 10 is similar to FIG. 9 and illustrates an example GUI 152 that displays an activation field view to the user via display 122 of programming device 110. From the defined stimulation field 158 on the side view 154 and cross-sectional view 156, processor 60 of programming device 110 may generate stimulation parameter values for therapy and generates an activation field model based upon the electrical field model 160 of FIG. 9 and a neuron model that estimates which neurons within the electrical field model will be activated by the voltage of the electrical field during therapy. The neuron model may be a set of equations, a lookup table, or another type of model that defines threshold action potentials of particular neurons that make up the anatomical structure, as defined by the patient anatomy data, affected by the electrical field 160. If the voltage or current amplitude of the electrical field 160 is above the threshold of any neuron within the electrical field, that neuron will be activated, e.g., cause a nerve impulse. The activation field model is displayed as activation fields 166 and 168 within stimulation field 158.

Activation fields 166 and 168 of the activation field model indicate to the user where neurons around the lead will be activated from the stimulation therapy. Due to changes in electrical current propagation and voltage thresholds to activate a neuron, the activation of neurons may vary with the location of tissue around the lead. Some neurons may activate further from the lead with smaller voltages while other neurons may only be activated close to the lead because of a high voltage threshold. These differences in neurons may account for separate activation fields 166 and 168 within a contiguous stimulation field 158.

The user may manipulate activation fields 166, 168 within GUI 152. For example, the user may increase or decrease the size and/or shape of activation fields 166 and 168 by changing the amplitude with amplitude 162 or directly manipulate (e.g., by modifying the borders of the displayed activation fields 166, 168) the activation fields to automatically modify the stimulation parameter values. Once the user is satisfied with activation fields 166, 168, the user may select accept field 164 to transmit the corresponding stimulation parameter values to IMD 14. In both GUI 150 (FIG. 9) and GUI 152 (FIG. 10), the user may view cross-sections at other electrode levels with arrows 170. If desired, activation fields 166, 168 may be stored as an algorithmic model of a baseline therapy field. For example, upon activation of accept field button 164, processor 60 may automatically store activation fields 166, 168 within therapy field models section 70 of memory 114 (FIG. 7).

GUIs 150, 152 also include scroll bars 136, 140, which are described with respect to FIG. 8. In the example shown in FIGS. 9 and 10, GUIs 150, 152 also present field menu button 172 to the user, which may present further options to a user. For example, upon activate menu button 172, the GUI 150, 152 may display a menu that enables a user to select a modify stimulation field button to redefine the stimulation field 158, select polarity button to alter the polarity of any of the electrodes, a change field view button to switch between electrical or activation field views 150, 152, and a manual mode button which allows the user to manually select the stimulation parameter values in an electrode view that displays the electrodes of the lead.

Although FIGS. 9 and 10 illustrate 2D views of lead 16, in other examples, a user interface may present a 3D view of lead 16 and the associated electrical field and activation fields may be displayed relative to the 3D views of lead 16.

Figure 11:
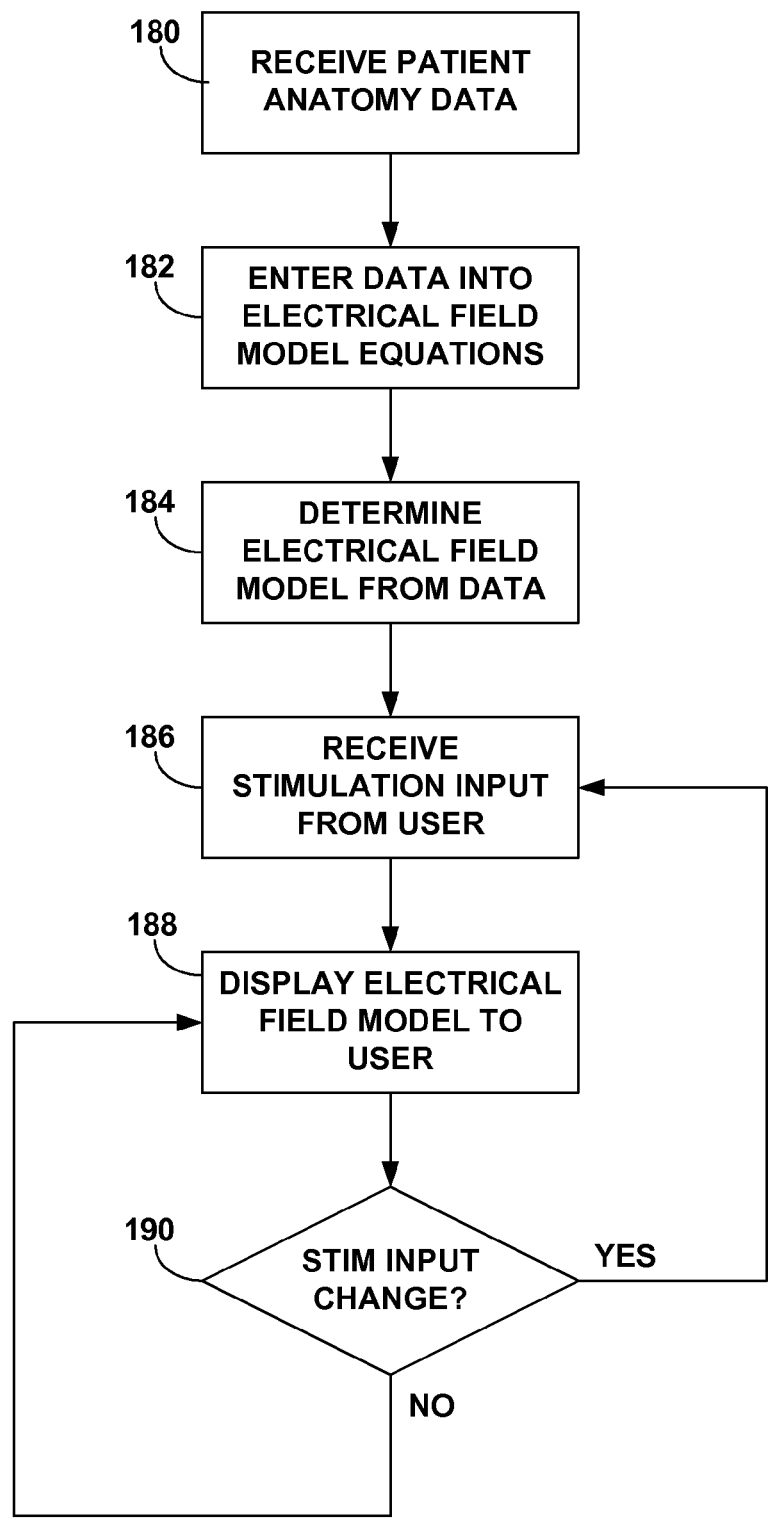
FIG. 11 is a flow diagram illustrating an example technique for determining and displaying an electrical field model, which may be stored as an algorithmic model of a baseline therapy field.

FIG. 11 is a flow diagram illustrating an example technique for determining and displaying electrical field model 160 (FIG. 9), which is based on a stimulation field 158. Stimulation field 158 may be determined based on input by a clinician and/or automatically generated by processor 60 of programming device 110 in response to stimulation parameter values selected by the clinician. As shown in FIG. 11, processor 60 receives patient anatomy data necessary for creating an electrical field (180), which may include an anatomical image of the target tissue site of patient 12, a reference anatomical image, which may not be specific to patient 12, an anatomical atlas indicating specific structures of the patient's anatomy or a map of the tissue characteristics (e.g., conductivity or density) adjacent to lead 16. As previously described, the patient anatomy data may be created based on a medical imaging technique, such as, but not limited to, CT and MRI data. Processor 60 may store the patient anatomy data within section 74 of memory 114 (FIG. 7).

Processor 60 may enter the patient anatomy data in stored electrical field model equations or equation sets to satisfy anatomical variable (182). Processor 60 may then determine the electrical field model from the data and equations (184). Once processor 60 receives stimulation input from a user defining the stimulation field, e.g., via user interface 112 (186), the electrical field may be displayed to the user via display 122 of user interface 112 (188). In some cases, processor 60 may receive an indication change in the stimulation input from a user (190), and the modified electrical field model (algorithmic model) may be presented to the user (188). The algorithmic model of the electrical field model displayed to the user (188) may be stored as an algorithmic model of a baseline therapy field within therapy field models section 70 of memory 114 (FIG. 7).

Figure 12:
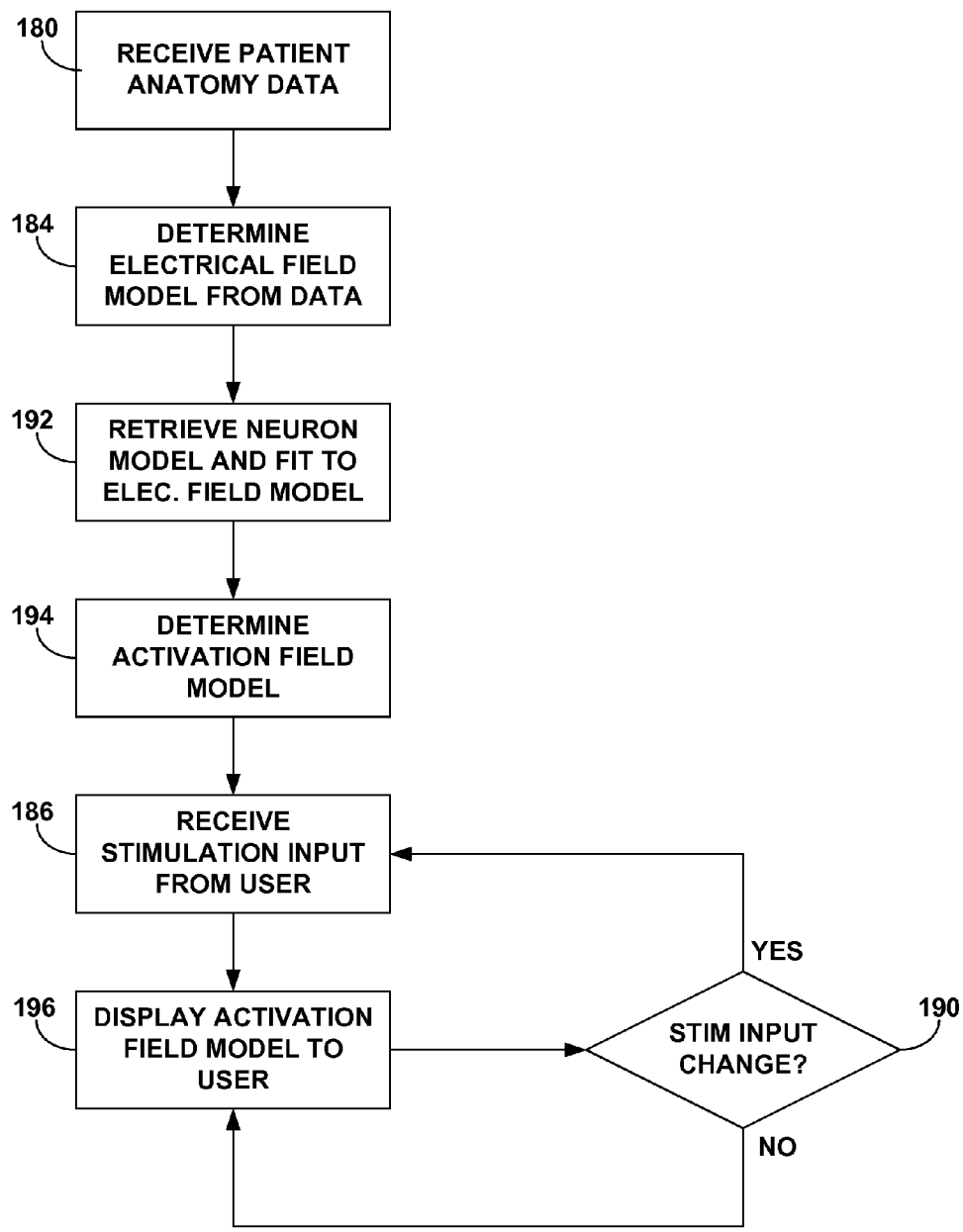
FIG. 12 is a flow diagram illustrating an example technique for determining and displaying an activation field model, which may be stored as an algorithmic model of a baseline therapy field.

FIG. 12 is a flow diagram illustrating an example technique for determining and displaying the activation field model of defined stimulation. As shown in FIG. 12, processor 60 receives patient anatomy data indicative of the anatomy of patient 12 (180) and processor 60 determines the electrical field model from the patient anatomy data (184). Processor 60 retrieves a neuron model from memory 114 (FIG. 7) and fits the neuron model to the electrical field model (192). The neuron model may be stored within patient anatomy data section 74 of memory 114 (FIG. 7). Processor 60 determines the activation field model based upon the electrical field model and neuron model (194).

Processor 60 may receive stimulation input from a user defining the stimulation field, e.g., via user interface 112 (186). Processor 60 may present the resulting activation field model to the user via display 122 (196). If the clinician desires to change the stimulation input (190), user interface 112 receives stimulation input from the clinician modifying the previous stimulation input (186). In some cases, processor 60 may receive an indication change in the stimulation input from a user (190), and the modified electrical activation field model may be presented to the user (196). The algorithmic model of the activation field model displayed to the user (196) may be stored as an algorithmic model of a baseline therapy field within therapy field models section 70 of memory 114 (FIG. 7).

The techniques shown in FIGS. 11 and 12 may also be used to generate an algorithmic model of a modified therapy field based on the modified therapy program (92) (FIG. 6). In particular, as described with respect to FIG. 6, in a technique for modifying a therapy program based on information indicative of a change in a therapy field, processor 60 of programmer 20 may modify a therapy program after receiving information indicative of a change in a therapy field, and generate an algorithmic model of a modified therapy field based on the modified therapy program. If the algorithmic model of the modified therapy field is an electrical field model, processor 60 may receive patient anatomy data (180), enter the patient anatomy data and the modified therapy program data into electrical field model equations (182), and determine an algorithmic model of an electrical field that is based on the modified therapy program (184) (FIG. 11). If the algorithmic model of the modified therapy field is an activation field model, processor 60 may receive patient anatomy data (180), enter the patient anatomy data and the modified therapy program data into electrical field model equations (182), determine the electrical field model based on the equations (184), and retrieve a neuron model and fit it to the electrical field model (192) in order to determine an activation field model based on the modified therapy program (194) (FIG. 12).

Figure 13:
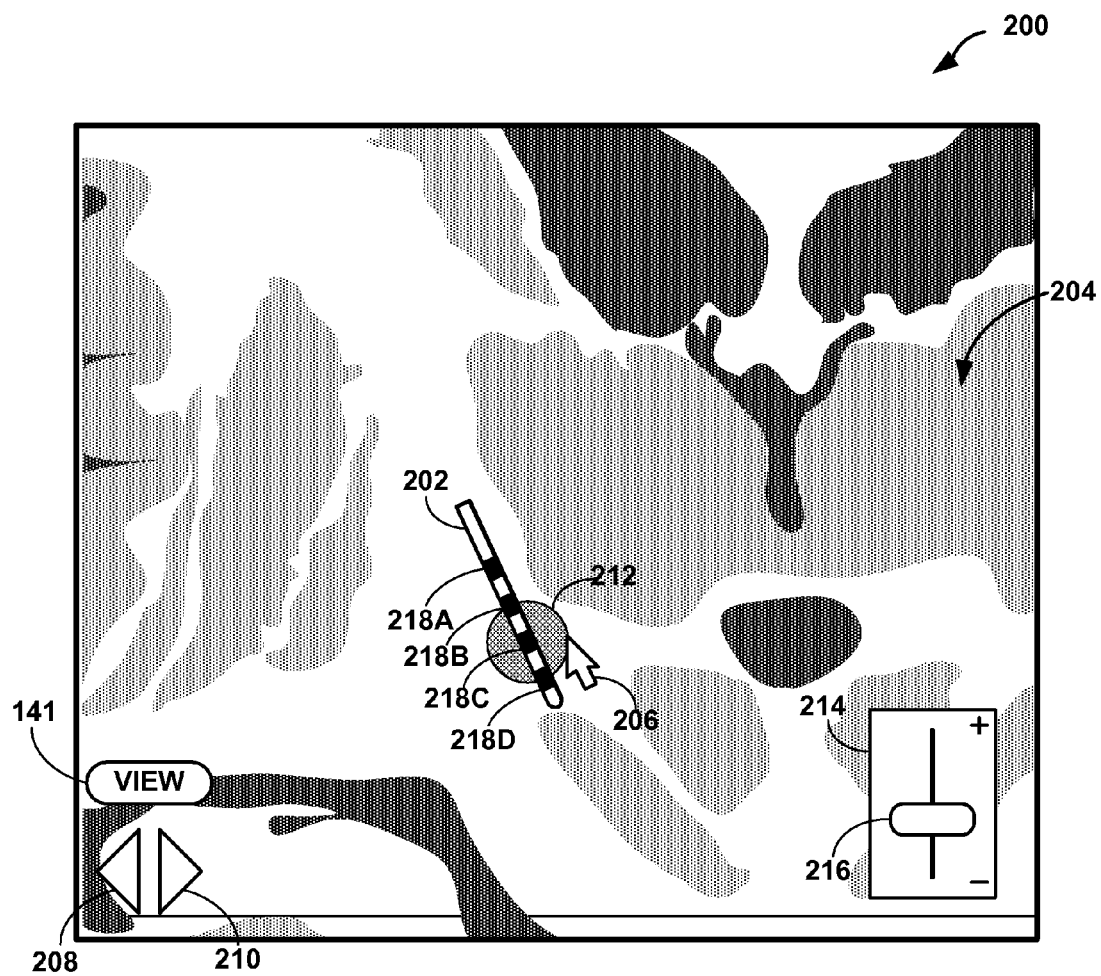
FIG. 13 illustrates an example GUI that may be presented on a display of a programming device.

An algorithmic model of a baseline therapy field, a present therapy field, a modified therapy field or another algorithmic model of a therapy field may also be generated using other techniques. FIG. 13 is a schematic illustration of another example of GUI 200 that may be presented on display 122 of programming device 110 in order to help a user generate an algorithmic model of a baseline therapy field. A user may interact with GUI 200 via user interface 112 of programming device 110 in order to generate an electrical field model and/or an activation field model. GUI 200 presents a representation of anatomical regions of brain 18. In GUI 200, a lead icon 202 representing lead 16 is displayed to illustrate where lead 16 is actually implanted relative to one or more anatomical regions of brain 18 of patient 12. In particular, GUI 200 displays coronal view 204 of brain 18, which is a front-back vertical section of brain 18, which includes lead icon 202. Coronal view 204 may be an actual image of brain 18 produced with magnetic resonance imaging (MRI), computed tomography (CT), or another imaging modality. These images are used to produce the anatomical regions needed to help the clinician program the stimulation parameter values.

Coronal view 204 is a 2D coronal slice of brain 18. Differently shaded portions of coronal view 204 indicate varying densities of tissue within brain 18. Darker portions indicate less dense tissue. For example, the darkest portion of coronal view 204 is indicative of spaces within brain 18 that contain cerebral spinal fluid (CSF). White portions of brain 18 indicate dense tissue and more neurons. The clinician may be able to recognize target anatomical regions by viewing coronal view 204. It should be noted that coronal view 204 shown in FIG. 13 is merely an example image, and actual images may include a wider range of shades and higher image resolution. Coronal view 204 provides a first perspective of the lead and the anatomical region in which the lead is implanted.

Coronal view 204 further includes pointer 206, previous arrow 208, next arrow 210, stimulation field 212, fine control input mechanism 214, and control slide 216. Pointer 206 may be controlled with a mouse and buttons, a track-ball, touch-pad, touch screen or other movement input device, which may be a part of user interface 112 of programming device 110. A user may use pointer 206 to drag lead icon 202 into position or rotate lead icon 202 within coronal view 204 to correctly orient the lead icon according to the actual position of lead 16 within brain 18. The actual position of lead 16 may be determined with the aid of medical imaging techniques, such as MRI or CT. In other examples, the user may first select the type of lead 16 implanted within patient 12 and select the correctly scaled size of lead icon 202 to correspond with the anatomical regions of coronal view 204.

Programmer 110 may initially orient the user to the middle depth of the coronal view 204 or another depth that the programmer automatically selects based upon the type of therapy, implant location, or some other simple indication of location. However, the user may use arrows 208 and 210 to move to another coronal depth where lead 16 is implanted in brain 18. The clinician may zoom in to or out of coronal view 204 for a larger view of anatomical regions of the coronal view. In addition, the clinician may move coronal view 204 up, down, left, or right to view a larger or smaller portion of brain 18. While the clinician may manually position lead icon 202 within coronal view 204, processor 60 may automatically position lead icon 202 within GUI 200 based upon stereotactic data that is generated before lead 16 is implanted within patient 12. A stereotactic frame may be placed on a cranium of patient 12 to specifically locate areas of brain 18. In addition, this stereotactic information may be used to provide coordinates of the exact location of the implanted lead 16. In other examples, brain 18 may be imaged after implantation of lead 16 such that the lead is identifiable on coronal view 204. The user may point to and identify electrodes of lead 16 in the image to allow programming device 110 to reconstruct the correct position of the lead 16. In some cases, programming device 110 may automatically identify lead 16 and place lead icon 202 correctly within the anatomical region without any input from the user.

GUI 200 allows the user to select and adjust one or more stimulation fields 212, which is a cross-sectional view of volumetric stimulation field, which may be further defined in other orthogonal views. In order to define stimulation field 212 within coronal view 204, the user may user pointer 206 to select one of electrode levels 218A, 218B, 218C or 218D for stimulation field 212. As with the lead shown in FIGS. 9 and 10, an electrode level may have one or more electrodes around the circumference of lead icon 202, e.g., a complex electrode array geometry. All circumferential electrodes of the selected electrode level are initially activated for programming. In some cases, the user may attempt to place stimulation field 212 over the anatomical regions targeted for stimulation therapy while avoiding anatomical regions that may initiate unwanted side effects. In some examples, stimulation field 212 may be a representation of an electrical field, current density, voltage gradient, or neuron activation, applied to a generic human tissue or the anatomy of patient 12. In addition, the clinician may be able to switch between any of these representations when desired.

In the example shown in FIG. 13, the user selected electrode level 218C and stimulation field 212 shows the anatomical region that would be stimulated with therapy delivery via the selected electrode level 218C. The user may use pointer 206 to drag stimulation field 212 to define a smaller or larger size, which corresponds to a lower or higher voltage or current amplitude. For example, the user may click on a border, or perimeter of stimulation field 212, and then drag the border to expand or contract the field 212. This adjustment is the coarse control of the size of stimulation field 212. The clinician may use pointer 206 to move control slide 216 up to slightly increase the size of stimulation field 212 or down to slightly decrease the size of stimulation field 212. In some examples, the actual voltage or current amplitude associated with stimulation field 212 is displayed on coronal view 204 as stimulation field 212 changes characteristics.

Processor 60 of programming device 110 may limit the rate of movement of stimulation field 212. In other words, stimulation field 212 may only be moved a certain number of steps per second within GUI 200, or any other user interface that allows the clinician to drag the stimulation field. This rate movement limit may prevent unnecessary calculations or ensure patient comfort in real-time changing of stimulation parameter values with modifications of stimulation field 212.

The initial size of stimulation field 212 may be determined by a minimal threshold voltage previously determined to provide some efficacious results to patient 12. In other examples, the initial stimulation field size may be small to allow the clinician to safely increase the size of stimulation field 212. The size of stimulation field 212 may be limited by a volume parameter value or a maximum voltage limit previously defined by the user or processor 60. The limit may be associated with capabilities of IMD 14 or safe voltage or current levels for patient 12. Once the size of stimulation field 212 is met, the clinician may no longer be able to drag the size of the stimulation field away from lead icon 202.

Stimulation field 212 may grow in size or split if the clinician selects more than one electrode level 218A-D. For example, the clinician may select electrode levels 218A and 218B to generate stimulation fields associated with each electrode level. The clinician may also move stimulation field 212 along the length of lead icon 202 and processor 60 may automatically select which electrode levels to activate to produce the stimulation field 212. The clinician may also move to other depths or slices of coronal view 204 with arrows 208 and 210. The other views may include, for example, a sagittal view of brain tissue, which may be taken from a perspective substantially perpendicular to the coronal view 204 or an axial view.

As described in further detail in U.S. patent application Ser. No. 11/591,299 to Stone et al., a programming device 110 may present a GUI including other views of brain 18 in addition to or instead of coronal view 240 in order to help select stimulation parameters for IMD 14. For example, programming device 110 may present a sagittal view of brain tissue or an axial view of brain tissue.

Figure 14:
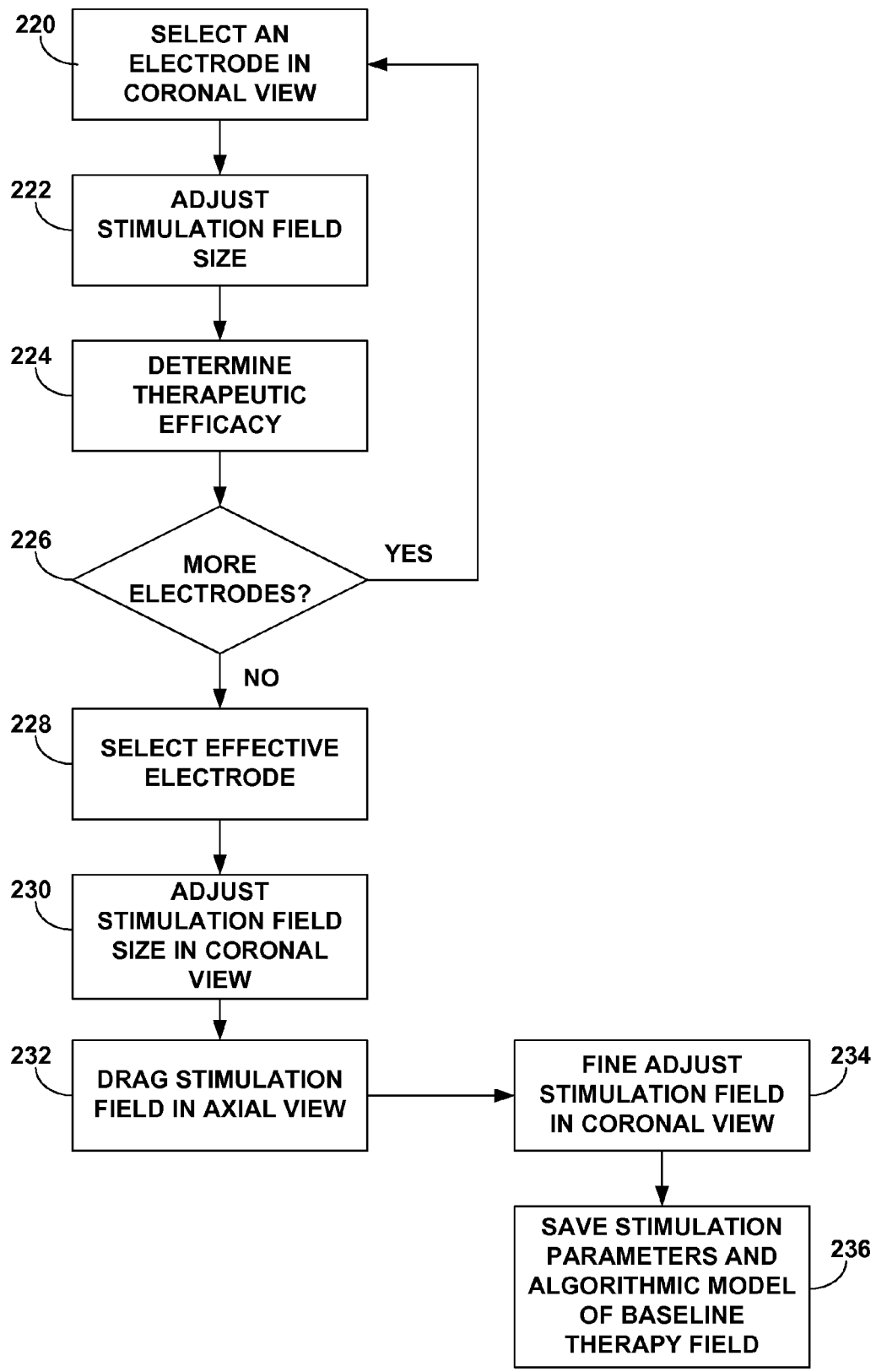
FIG. 14 is a flow diagram illustrating an example technique for adjusting a stimulation field for stimulation therapy in order to define stimulation parameter values and generate an algorithmic model of a baseline therapy field.

FIG. 14 is a flow diagram illustrating an example technique for adjusting stimulation field 212 for stimulation therapy in order to define stimulation parameter values for IMD 14 and to generate an algorithmic model of a baseline therapy field. As shown in FIG. 14, the clinician begins by selecting an electrode level 218A-D in coronal view 204 of GUI 200, although other views, such as a sagittal view or axial view of brain 18 may also be used to select an electrode level 218A-D (220). Processor 60 activates all the electrodes, i.e., electrodes at different angular positions around the lead circumference, in the selected electrode level. The user may interact with GUI 200 in order to adjust a size of stimulation field 212 (222) and test the stimulation field 212 on patient 12 to determine the therapeutic effect, if any (224). If the user wants to test stimulation delivered by more electrode levels (226), the user may repeat this process by selecting another electrode level and testing it on patient 12.

If there are no more electrode levels to test, the user may select the most effective electrode level from the tested electrodes (228) and adjust the size of stimulation field 212 by interacting with GUI 200 (230). The user may drag stimulation field 212 within GUI 200 in order to define a field 212 that minimizes side effects and maximizes therapeutic benefits to patient 12 (232). In addition, the user may use fine adjustment buttons 214 and 216 to further adjust stimulation field 212 (234). Additionally, the clinician may use a wand tool to select a range of pixel shades to quickly select anatomical regions that will be included in stimulation field 212.

In some examples, the user may adjust the simulation field in any of sagittal, coronal, or axial field views as desired by the clinician. In other examples, GUI 200 may require that the clinician enters each of the sagittal, coronal, and axial field views at least once before adjustment of the stimulation can be completed. Once stimulation field 212 is adjusted to produce effective therapy for patient 12, the user may save the electrode configuration and other stimulation parameter values that achieve the stimulation field 212 as a stimulation program within memory 114 (FIG. 7) (236). The stimulation field 212 may also be stored as an algorithmic model of a baseline therapy field (236). Processor 60 may control the transmission of the therapy program to IMD 14 via telemetry device 66 (FIG. 7). In some examples, the user may repeat the programming procedure with GUI 200 to generate multiple stimulation programs and respective algorithmic models of baseline therapy fields. The clinician may also reprogram the therapy at any time with the aid of GUI 200 and generate an algorithmic model of a baseline stimulation field based on the reprogrammed therapy program.

Processor 60 of programming device 110 may use information received via user interface 112 to automatically generate stimulation parameter values according to the stimulation field 212 defined by the user. Processor 60 determines the dimensions of the stimulation field 212 to create a 3D vector field identifying the distances from lead 16 that stimulation may reach. Processor 60 may utilize the 3D vector field with an equation approximating electrical current propagation within brain tissue. The resulting data determines the electrode combination, voltage and current amplitudes, pulse rates, pulse widths, and, in some cases, other stimulation parameter values (e.g., duty cycle values) needed for reproducing the stimulation field within patient 12. In other examples, processor 60 of programmer 110 interprets density of tissue in the imaging data to more precisely approximate the stimulation parameter values.

In some examples, processor 60 may utilize one or more stimulation templates stored within memory 114 in order to generate the stimulation parameter values for achieving the stimulation field 212 defined by the user. As previously described, a stimulation template may be a predetermined volumetric stimulation field that processor 60 may match to a desired stimulation field 212. Each stimulation template may be based upon any one or combination of modeled data, experimental data, or analytical calculations prior to being stored in programming device 114. Stimulation templates are described in further detail in U.S. patent application Ser. No. 11/891,299 to Stone et al.

In other examples, a user may generate an algorithmic model of a stimulation field 212 without the aid of a lead icon 202. For example, when presented with the coronal view of the brain, as shown in FIG. 13, the user may create an outline defining the outer edges of stimulation field 212. By defining an algorithmic model of stimulation field 212 by outlining the desired field within GUI 200, the user outlining desired areas includes allowing the user to focus on the anatomy and physiology of patient 12 instead of manipulating an implanted device. Consequently, automatically generating stimulation parameter values according to a user-selected stimulation area (or volume) may increase therapy efficacy and decrease programming time.

In addition, in other examples, a user may select stimulation parameter values and generate an algorithmic model of a baseline therapy field that indicates the field that provides efficacious therapy to patient 12 with the aid of an atlas of an anatomical region of patient 12. The atlas may be represented in the form of a drawing or actual image from an imaging modality such as magnetic resonance imaging (MRI), computer-aided tomography (CT), or other similar imaging technique. The reference anatomy may be an anatomy different from patient 12 anatomy. Specific structures of the reference anatomy may be identified and their locations within the reference anatomy determined to create an atlas. The atlas may be stored in memory 114 of programming device 110. While an atlas may differ from the actual patient anatomy, the structure locations may be close enough to provide guidance to a user to generate stimulation parameter values based upon the atlas.

In addition, in some examples, the user may generate an algorithmic model of a baseline therapy field with the aid of a user interface that presents, at the same time, an atlas and the actual anatomy of patient 12, e.g., generated by a suitable medical imaging technique. The atlas of the reference anatomy and the patient-specific anatomy may be combined to create a morphed atlas for programming the stimulation therapy. One example of how programming device 110 may create a morphed atlas is described in U.S. Patent Application No. 2005/0070781 by Dawant et al., entitled, "ELECTROPHYSIOLOGICAL ATLAS AND APPLICATIONS OF SAME" and filed Jul. 1, 2004.

Examples of systems and techniques for selecting therapy parameter values and generating a resulting stimulation field with the aid of an atlas is described in further detail in U.S. patent application Ser. No. 11/891,299 to Stone et al. In one technique described by U.S. patent application Ser. No. 11/891,299 to Stone et al., a user may use a pointer to select a specific structure of the atlas presented on a user interface of a programming device, and the name of the structure may be is displayed. The programming device may generate stimulation parameter values based upon the location of the one or more selected structures to the location of the implanted lead. In some examples described by U.S. patent application Ser. No. 11/891,299 to Stone et al., generating stimulation parameter values may include selection of stimulation templates and creation of a stimulation template set based on the selected structures. An atlas may allow a clinician to quickly select the most appropriate structure that needs to be stimulated to treat the condition of patient.

Figure 15:
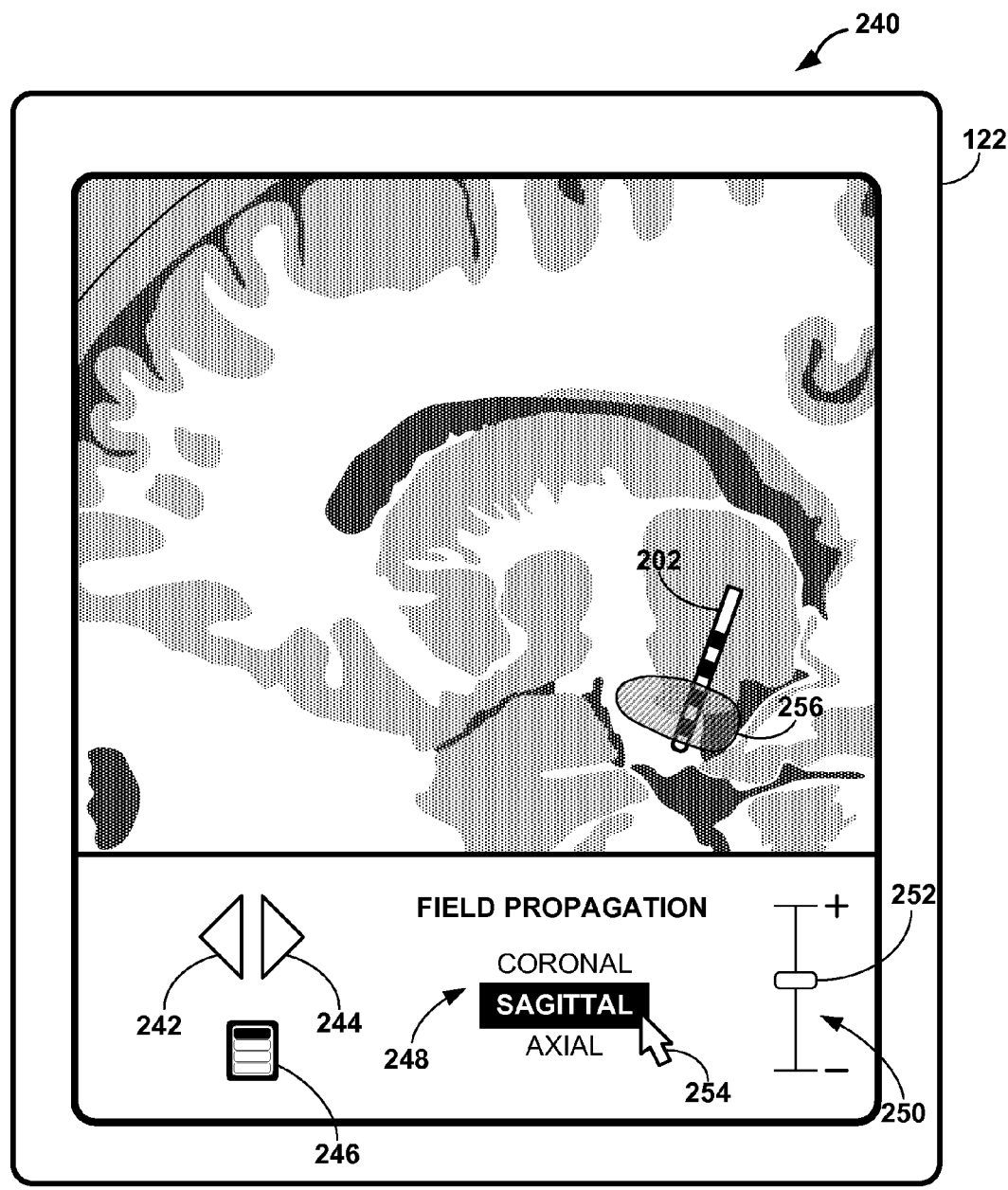
FIG. 15 illustrates an example GUI that may be presented on a display of a programming device.

Just as with GUIs 150, 152, an electrical field model or an activation field model may be generated based on a selected stimulation field 212. The electrical field model may approximate actual stimulation effects from therapy. FIG. 15 is an example screen shot of a GUI 240 that presents a sagittal view of a patient anatomy with an algorithmic model of an electrical field 256 of the defined stimulation therapy. Processor 60 may control the display of GUI 240 on display 122 (FIG. 7). The sagittal view of the patient anatomy may be a 2D view of any one of an atlas, a morphed atlas, or a patient anatomical region. GUI 240 also includes previous arrow 242, next arrow 244, menu 246, view indicator 248, and amplitude adjuster 250 with slider 252. In the example shown in FIG. 15, the clinician interacts with GUI using pointer 254, which may be similar to pointer 206 (FIG. 13).

Processor 60 of programming device 110 controls GUI 240 to display lead icon 202 and electrical field 256 to present an illustration to the clinician of what the electrical field of the stimulation therapy would look like according to the stimulation parameter values defined by the clinician using any of the programming techniques described herein. Electrical field 256 is an algorithmic model that represents where the electrical current will propagate from lead 16 within brain 18, as tissue variation within brain 18 may change the electrical current propagation from the lead. The variations in electrical field propagation may affect the ability of the therapy to actually treat a desired structure or cause a side effect.

Electrical field 256 is a 2D slice of the volumetric electrical field model created by programming device 110. Processor 60 utilizes the patient anatomical region data with electrical field model equations that define current propagation. Accordingly, electrical field 256 is an algorithmic model of an electrical field that indicates where stimulation will propagate from an implanted lead (represented within GUI 240 by lead icon 202). The clinician may interact with GUI 240 to increase or decrease the amplitude of the stimulation parameter values with amplitude adjuster 250 and view how the amplitude change would affect the size and shape of electrical field 256. Amplitude adjuster 250 is an analog adjustment mechanism and may also be in the form of an adjustment knob instead of the slider. The user may move to different depths of the sagittal view with previous arrow 242 or next arrow 244 while adjusting the amplitude of electrical field 256 with slider 252. In some examples, GUI 240 may allow the user to redefine the stimulation field and generate new stimulation parameter values if it is believed that electrical field 256 is unacceptable for therapy. Algorithmic model of electrical field 256 may be generated using a technique similar to that shown in FIG. 11.

Figure 16:
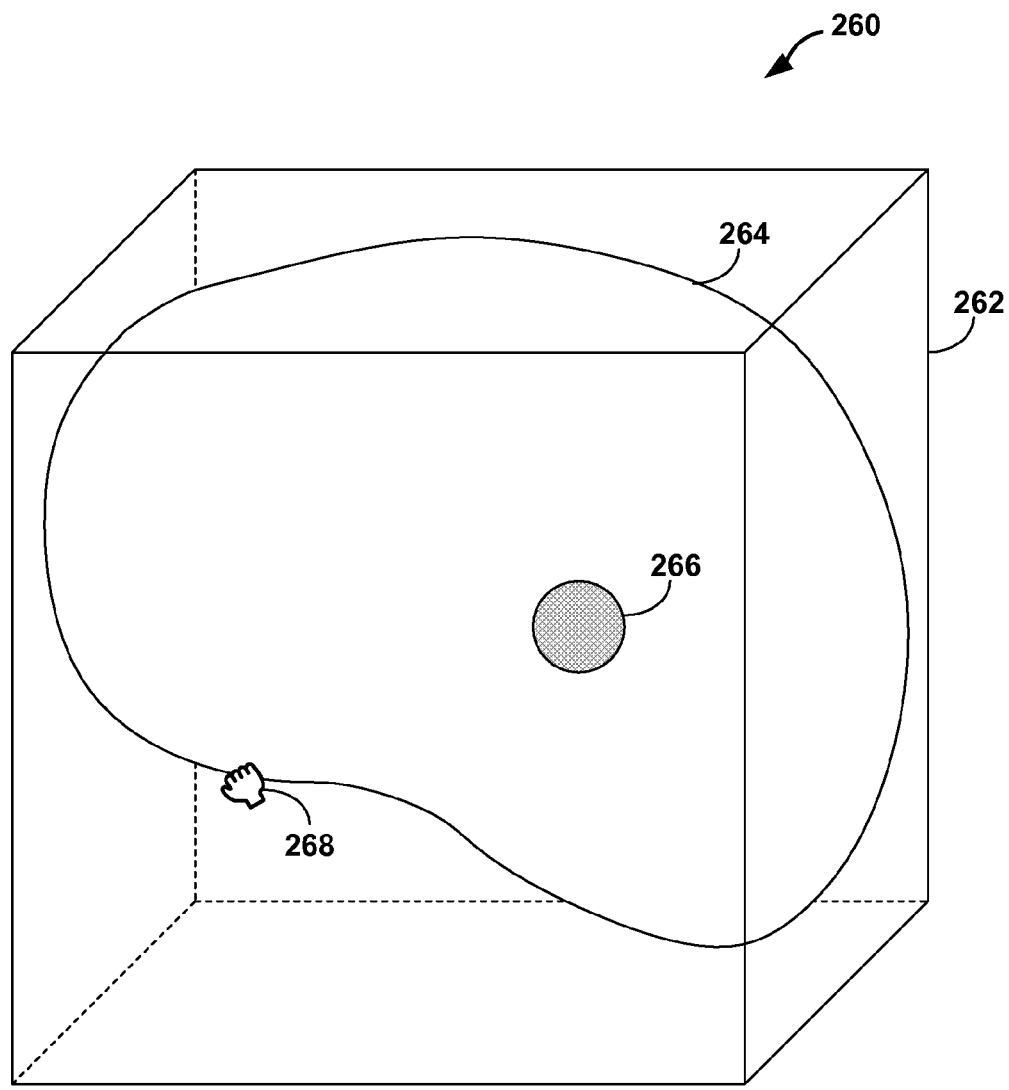
FIG. 16 is a conceptual diagram illustrating a three-dimensional (3D) visualization environment including a 3D brain model for defining a 3D stimulation field and an algorithmic model of a baseline therapy field.

An algorithmic model of a therapy field, such as a baseline therapy field, a present therapy field based on a current therapy program and information indicative of a change in a therapy field or a modified therapy field based on a modified therapy program, may also be generated within a 3D environment. FIG. 16 is a conceptual diagram illustrating a 3D visualization environment including a 3D brain model for defining a 3D stimulation field. As shown in FIG. 16, GUI 260 presents a 3D environment 262 that illustrates brain model 264, stimulation field 266, and hand 268. Stimulation field 266 may be stored as an algorithmic model of a baseline therapy field, where stimulation field 266 is generated based on patient anatomy, hardware characteristics of therapy system 10, and the stimulation parameter values. However, in some cases, the stimulation parameter values may be selected to achieve stimulation field 266. Thus, in such cases, stimulation field 266 may be generated based on patient anatomy and hardware characteristics of therapy system 10. GUI 260 may be presented by processor 60 on display 122 of programming device 110. Brain model 264 is a 3D anatomical region and stimulation field 266 is a 3D stimulation field displayed relative to brain model 264. A user may interact with GUI 200 to move hand 268 in order to control the view and aspects of 3D environment 262. In the example shown in FIG. 16, brain model 264 is positioned to illustrate a sagittal view.

3D environment 262 may be displayed on a 2D display by using partially transparent surfaces and grey or color shades. A fully interactive 3D environment 262 may allow a clinician to view within brain model 264 and identify anatomical regions that are targets for stimulation therapy. Brain model 264 may be generated from imaging data from MRI, CT, or another medical imaging modality. While shading of brain model 264 is not shown in FIG. 16, brain model 264 may include shading or other techniques for illustrating different anatomical regions of brain 18.

While a lead icon representing lead 16 is not shown within 3D environment 262, processor 60 may incorporate imaging data into 3D environment 262 after lead 16 is implanted. That is, processor 60 may automatically recognize the orientation and location of lead 16 within patient 12 based on imaging data input into programming device 110, and may present a lead icon within GUI 260 based on the actual orientation and location of lead 16 within patient 12. Alternatively, the user may manually place a lead icon within 3D environment 262 based upon stereotactic data or implant coordinates for the actual lead 16 implanted within patient 12.

Processor 60 may control the presentation of GUI 260 and select the location of stimulation field 266 based upon the implant site of lead 16 within patient 12. A user may then interact with GUI 260 to adjust and manipulate stimulation field 266 as desired with hand 268 or other input mechanisms provided by user interface 112 of programming device 110 (FIG. 7). The user may also use hand 268 to rotate and spin brain model 264 in any direction. GUI 260 may support zooming in and out relative to brain model 264, as well as displaying different perspectives of brain model 264 within 3D environment 262 to see stimulation field 266 within brain model 264 from different perspectives.

GUI 260 may include a wand tool that allows the user to highlight various regions of brain model 264 to be included in stimulation field 266. The wand tool may automatically select voxels (i.e., pixels in all three dimensions). In other dimensions, the clinician may grab one of several predefined stimulation field shapes and place the shape within brain model 264 to become stimulation field 266 or select specific brain structures for stimulation. In any case, GUI 260 may set limits to stimulation field 266 based upon the characteristics of lead 16 and the capabilities of IMD 14. Patient 12 safety may also govern the size and location of stimulation field 266.

Figure 17:
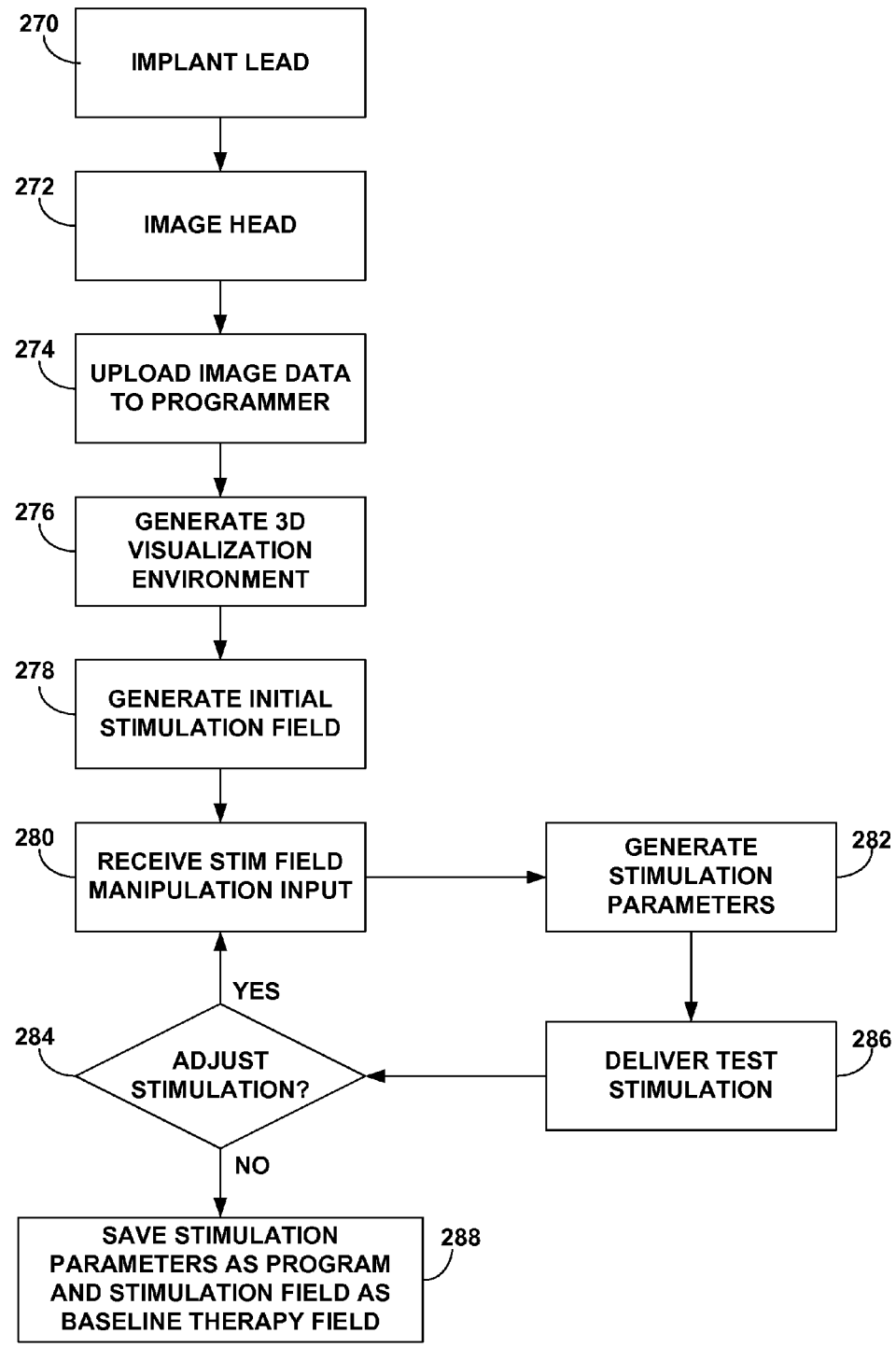
FIG. 17 is a flow diagram illustrating an example technique for defining a 3D stimulation field within a 3D brain model of patient 12.

FIG. 17 is a flow diagram illustrating an example technique for defining a 3D stimulation field within a 3D brain model of patient 12. As shown in FIG. 17, a user, such as a clinician, may implant lead 16 within brain 18 using any suitable technique, such as a stereotactic technique (270). The clinician may images the head of patient 12 to obtain data of brain 18 necessary for generating the brain model 264 (272). The clinician may upload the image data to a computing device, such as programming device 110 (274). The image data may be stored within patient anatomy data section 74 of memory 114 (FIG. 7). Processor 60 of programming device 110 may generate a 3D environment (276) and generate brain model 264 and the initial stimulation field 266 within the 3D environment (278). The initial stimulation field may be generated with a set of stimulation parameter values that are believed to provide efficacious therapy to patient 12 for the particular patient condition. These initial stimulation parameter values may be specific to patient 12 or may be general to more than one patient.

With the aid of user interface 112, processor 60 may receive stimulation field input from a clinician, such as adjustments and manipulations to stimulation field 2566 within the 3D environment (280). Processor 60 may generate stimulation parameter values according to the stimulation field 266 resulting from the adjustments and manipulations from the user (282) and control IMD 14 to deliver test stimulation with the parameter values (286). If the clinician desires to adjust stimulation parameter values (284) based on the feedback from patient 12 and/or sensors, processor 60 may continue receiving stimulation field input (280) and testing the stimulation according to the modification to stimulation field 266 (282, 286). If the stimulation therapy is effective, the clinician may save the stimulation parameter values in IMD 14 so that patient 12 can receive therapy with the parameter values (288). In addition, stimulation field 266 may be stored within IMD 14 or programming device 110 as a baseline therapy field model.

In addition to or instead of using stimulation field 266 as an algorithmic model of a therapy field, such as a baseline therapy field, present therapy field or a modified therapy field, an electrical field model and/or activation model may be generated based on stimulation field 266 and stored as an algorithmic model of a therapy field. The electrical field model and activation field model may be generated by processor 60 using any suitable technique, such as the techniques shown in FIGS. 11 and 12, and displayed within 3D environment 262 using any suitable technique, such as those described in U.S. patent application Ser. No. 11/891,299 to Stone et al. The clinician or other user may modify the stimulation parameter values by directly modifying the size, shape or location of the electrical field model or activation field model within 3D environment 262, or the clinician may modify the electrical field model or activation field model may directly modifying the stimulation parameter values.

Figure 18:
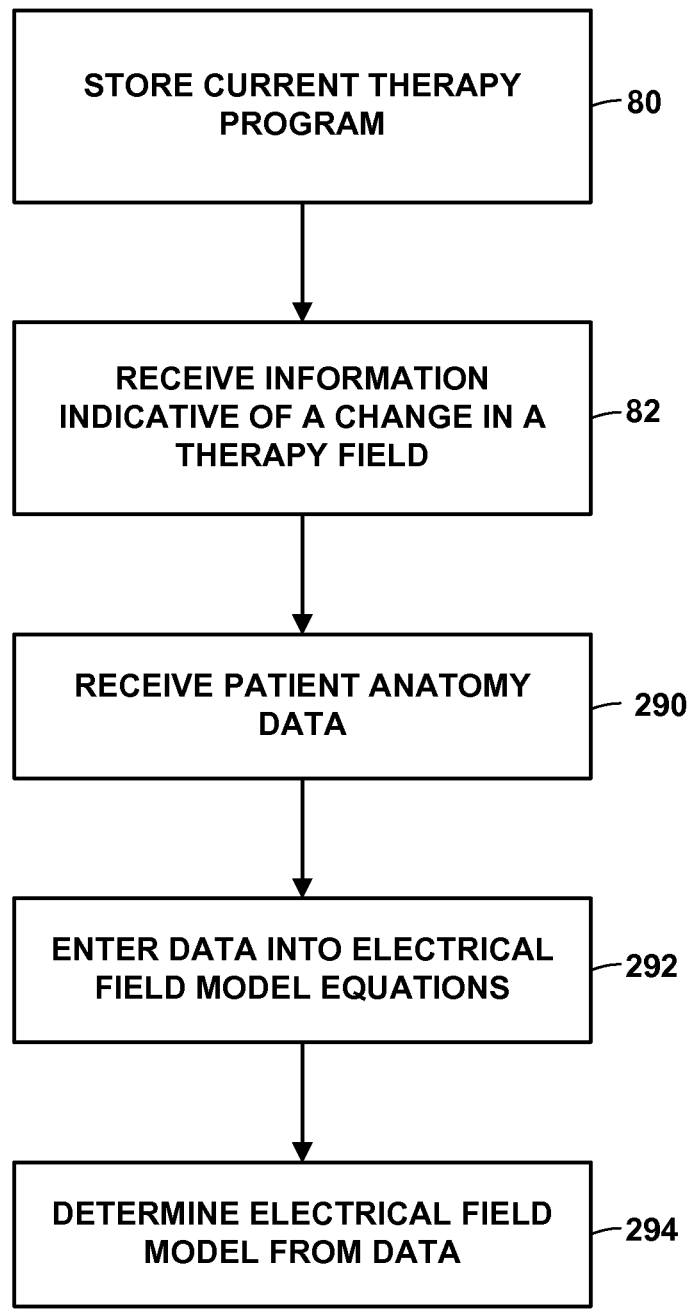
FIG. 18 is a flow diagram illustrating an example technique for generating the algorithmic model of a present therapy field upon receiving information indicative of a change in a therapy field.

As discussed with respect to FIG. 4, in one example technique for modifying a therapy program based on information indicative of a change in a therapy field, processor 60 of programming device 110 (or programmer 20) generates an algorithmic model of a present therapy field based on information indicative of a change in a therapy field and a therapy program currently implemented by IMD 14. FIG. 18 is a flow diagram illustrating an example technique for generating the algorithmic model of a present therapy field, where the algorithmic model is an electrical field model. In other examples, processor 60 may generate an activation field model in addition to or instead of the electrical field model in order to generate the algorithmic model of a present therapy field.

As discussed with respect to FIG. 4, processor 60 may store the current therapy program implemented by IMD 14 (80), which may be the therapy program determined to provide efficacious therapy to patient 12 during a programming session. Processor 60 may receive information indicative of a change in a therapy field (82), which may include a change in the hardware characteristics of a therapy system that may affect the stimulation delivered to patient 12. Processor 60 may receive patient anatomy data (290), such as by retrieving the data from the stored data 94 (FIG. 7).

Processor 60 enters the patient anatomy data, which may include the location and orientation of the implanted lead 16 or leads 34, 36 within patient 12, the current therapy program, and the information indicative of the change in the hardware characteristics into electrical field model equations that define how the electrical field is propagated from an origin location, e.g., the electrodes of the one or more implanted leads (292). Processor 60 then determines the estimated electrical field that will be produced in therapy to generate the algorithmic model of the electrical field (294). In some cases, processor 60 presents the electrical field model to a user via display 122.

The electrical field model equations may determine how the information indicative of a change in a therapy field affects the electrical field that results from therapy delivery according to the current therapy program. For example, if the information indicative of a change in a therapy field indicates that one of the electrodes of the therapy program's electrode combination is faulty and does not transmit the stimulation signals to target tissue, the electrical field model equations may implement an algorithm that assumes zero or minimal stimulation is delivered from the faulty electrode in order to generate an electrical field model that reflects the electrical field resulting from therapy delivery with the faulty electrode. As another example, if the information indicative of a change in a therapy field indicates that leads 34, 36 have moved relative to each other and indicates the actual distance D (FIG. 1B) between the implanted electrodes 35, 37, the electrical field model equations may implement an algorithm that estimates how the electrical field propagates from the electrodes that are spaced the distance D from each other.

While the description primarily refers to electrical stimulation therapy, in some cases, the therapy field resulting from the delivery of a therapeutic agent to a target tissue site within patient may be used to modify a therapy program. In the case of therapeutic agent delivery, the therapy parameters may include the dosage of the therapeutic agent (e.g., a bolus size or concentration), the rate of delivery of the therapeutic agent, the maximum acceptable dose in each bolus, a time interval at which a dose of the therapeutic agent may be delivered to a patient (lock-out interval), and so forth. Accordingly, information indicative of a change in a therapy field may indicate characteristics, such as the location and orientation, of other therapy delivery elements in addition to or instead of medical leads, such as catheters, microstimulators, and the like. Example therapeutic agents include, but are not limited to, pharmaceutical agents, insulin, pain relieving agents, anti-inflammatory agents, gene therapy agents, or the like.

Just as with the stimulation systems 10, 30 described above, for a therapy system that includes delivery of a therapeutic agent, an algorithmic model of a therapy field may be generated with the aid of modeling software, hardware or firmware executing on a computing device, such as programmer 20 or a separate dedicated or multifunction computing device. An algorithmic model of the baseline therapy field may be a known therapy field that results from delivery of a therapeutic agent to a target tissue site according to at least one therapy program determined to deliver efficacious therapy to the patient, and is also based on an anatomical data set, such as tissue density data, body fluid pressure, body fluid flow rates, body fluid diffusion rates, and effective duration of the therapeutic agent on the target tissue. Again, the anatomical data set may be specific to the patient or may be general to more than one patient. The anatomical data set comprises at least one of an anatomical image of a patient, a reference anatomical image, an anatomical atlas or a tissue conductivity data set.

In some cases, the algorithmic model of a therapy field resulting from delivery of a therapeutic agent may indicate the anatomic structures or the tissue area that are affected by the therapeutic agent. For example, if the therapeutic agent delivers a genetic material to a target tissue site within a patient, where the genetic material causes transgene expression by tissue at the stimulation site, the therapy field may indicate the region of tissue that results in the transgene expression. The transgene expression may include an increased expression of proteins, such as connexins, gap junctions, and ion channels, to increase the conductivity of the tissue at the target tissue site, or the delivered genetic material may cause expression of a metalloproteinase, an anti-inflammatory agent, or an immunosuppressant agent.

As another example, if the therapeutic agent delivers a pain relieving agent to a target tissue site within a patient, the algorithmic model of the therapy field may indicate the region of tissue that absorbs the pain relieving agent and/or the region of paresthesia or other physiological effects that may result from delivery of the therapeutic agent to the target tissue site.

In the case of for a therapy system that includes delivery of a therapeutic agent, information indicative of a change in a therapy field may include information relating to the flow of fluid from the medical device and/or through a therapy delivery element (e.g., a catheter) that delivers the therapeutic agent to a target tissue site within the patient. For example, the therapy delivery element may define a fluid outlet that becomes blocked due to tissue in-growth. The blocked fluid outlet may affect the flow rate from the fluid reservoir within the medical device, which may signal to the medical device or programming device 110 that there has been a change to the therapy field due to a reduction in fluid flow. A flow meter may be positioned within the therapy delivery element or the medical device to measure fluid flow.

In addition or instead of information indicative of a blocked fluid outlet, the information indicative of a change in a therapy field may include any information indicating the therapy delivery element is constricted. The constrictions on the therapy delivery element may be attributable to, for example, changes in the patient's anatomy, movement of the therapy delivery element within the patient to a region that is susceptible to more constrictions (e.g., a catheter pinched between joints), tissue in-growth, kinks in the therapy delivery element (e.g., from a twisting movement within the patient), and the like. Other information indicative of a change in a therapy field may include information indicating movement of the therapy delivery element within patient 12. Movement of the therapy delivery element may be detected via, e.g., electrodes on the therapy delivery element, which may be useful for measuring the therapy delivery element position relative to a reference point (e.g., a medical device), an accelerometer on the therapy delivery element that indicates a change in position of the therapy delivery element relative to a reference point or by a medical imaging technique.

Other information indicative of a change in a therapy field resulting from delivery of one or more therapeutic agents may include, for example, biomarkers measured at the target tissue site or at another region of the patient's body. The biomarkers may include, for example, the pH, impedance of the tissue, fluid pressure or other measures that would be indicative of the drug concentration within patient 12.

The algorithm for generating an algorithmic model of a therapy field resulting from delivery of one or more therapeutic agents may be generated with the aid of computer modeling techniques. The algorithmic model of the therapy field may indicate the diffusion of the therapeutic agent through the patient's body from a therapy delivery element. The algorithmic model may be an algorithmic model that is generated based on a patient anatomy, the patient's tissue characteristics, and therapeutic agent delivery parameter values. In one example, the algorithm includes equations that define drug propagation through the patient's tissue based on the physical tissue characteristics (e.g., density) and body fluid flow, pressure, and diffusion characteristics adjacent the therapy delivery element. The drug propagation equations may be specific to patient 12 or may be based on information not specific to patient 12. From this information, processor 60 of programming device 110 may be able to generate the estimated therapeutic agent propagation field that will be produced in therapy.

In relatively static body fluids, such as like the spinal cord fluid (SCF), the drug propagation equations may define a simple diffusion model coupled with a model of the therapeutic agent's effective duration within the patient's body. Physiological parameters such a pressure at the target tissue site may impact the diffusion rate. In relatively fluid body fluids, such as the blood stream, the drug propagation equations may define a diffusion model that also considers the body fluid pressure as well as the body fluid flow rate. Generally, these body fluid characteristics, such as flow rate and pressure, may change relatively quickly for a patient, e.g., based on hydration, heart rate, and the like. Accordingly, sensors may be used to regularly determine the body fluid characteristics, and provide feedback to processor 60 (or a processor of the therapeutic agent delivery device or another device), which may then generate an algorithmic model of the diffusion of the therapeutic agent and determine whether one or more parameter values of the therapeutic agent delivery are desirable based on the modeled diffusion.

The techniques described in this disclosure, including those attributed to IMD 14, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 14 and/or processor 60 of programmer 20, any one or more parts of the techniques described herein may be implemented by a processor of one of IMD 14 or programmer 20, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

The invention claimed is:

1. A method comprising:
   receiving, with one or more processors, information indicative of a change in a first therapy field, wherein the first therapy field was generated by prior delivery of therapy, by a medical device, to tissue of a patient according to a therapy program, wherein prior to the change in the first therapy field, when the medical device delivers therapy according to the therapy program, the first therapy field is generated, and wherein the change in the first therapy field occurs without change to the therapy program;
   in response to receiving the information indicative of the change in the first therapy field, generating, with the one or more processors, a first therapy field model based on the therapy program that is used to generate the first therapy field prior to the change in the first therapy field and the information indicative of the change in the first therapy field;
   comparing, with the one or more processors, the first therapy field model to an algorithmic model of a baseline therapy field; and
   modifying, with the one or more processors, the therapy program based on the comparison of the first therapy field model to the algorithmic model of the baseline therapy field.

2. The method of claim 1, wherein the therapy is delivered to the patient, by the medical device, via a plurality of electrodes, and receiving the information indicative of the change in the first therapy field comprises detecting an impedance change of at least one electrode of the plurality of electrodes.

3. The method of claim 2, wherein generating the first therapy field model comprises generating the first therapy field model based on the therapy program and the impedance change of the at least one electrode.

4. The method of claim 1, wherein the therapy is delivered to the patient, by the medical device, via a plurality of electrodes, and receiving the information indicative of the change in the first therapy field comprises detecting an open circuit condition of at least one electrode of the plurality of electrodes.

5. The method of claim 1, wherein the therapy is delivered to the patient, by the medical device, via a plurality of electrodes, and receiving the information indicative of the change in the first therapy field comprises detecting movement of at least one electrode of the plurality of electrodes relative to a target tissue site within the patient.

6. The method of claim 1, wherein receiving the information indicative of the change in the first therapy field comprises detecting a change in a hardware characteristic of the medical device.

7. The method of claim 1, wherein generating the first therapy field model based on the therapy program and the information indicative of the change in the first therapy field comprises:
   receiving patient anatomy data; and
   entering the patient anatomy data and the information indicative of the change in the first therapy field into an electrical field model equation that defines how an electrical field will propagate through the tissue from an implant system comprising the medical device delivering the therapy according to the first therapy program.

8. The method of claim 1, wherein comparing the first therapy field model to the algorithmic model of the baseline therapy field comprises comparing at least one field characteristic of the first therapy field model and the algorithmic model of the baseline therapy field.

9. The method of claim 8, wherein the field characteristic comprises at least one of stimulation volume, a centroid of stimulation, activated neurons, an amplitude of the voltage or current at a spatial point within the stimulation volume or a charge density.

10. The method of claim 1, wherein modifying the therapy program comprises modifying the therapy program to substantially maintain at least one field characteristic of the baseline therapy field.

11. The method of claim 1, wherein modifying the therapy program results in a modified therapy program, the method further comprising determining an efficacy of the modified therapy program.

12. The method of claim 1, further comprising generating the algorithmic model of the baseline therapy field, wherein generating the algorithmic model of the baseline therapy field comprises:
   receiving patient anatomy data that describes at least one characteristic of the tissue of the patient proximate to a therapy delivery element implanted within the patient and coupled to the medical device;

receiving user input indicating at least one of a configuration or a location of the therapy delivery element;

receiving user input indicating at least one therapy parameter value for therapy delivery via the therapy delivery element; and generating the algorithmic model of the baseline therapy field that represents where at least one of electrical stimulation or therapeutic agent delivery will propagate from the therapy delivery element based on the patient anatomy data, the configuration of the at least one therapy delivery element, and the at least one therapy parameter value.

13. The method of claim 1, further comprising generating the algorithmic model of the baseline therapy field, wherein generating the algorithmic model of the baseline therapy field comprises generating the algorithmic model of at least one of an electrical field, an activation field, a voltage gradient or a current density that provides efficacious therapy to the patient.

14. The method of claim 1, wherein the baseline therapy field comprises a known therapy field that results from delivery of stimulation according to at least one therapy program determined to deliver efficacious therapy.

15. The method of claim 1, further comprising:
controlling the medical device to deliver therapy according to the modified therapy program.

16. A system comprising:
an implantable medical device configured to deliver therapy to tissue of a patient according to a therapy program, wherein when the implantable medical device delivers therapy according to the therapy program a first therapy field is generated within the tissue; and
a processor configured to:
receive information indicative of a change in the first therapy field after the generation of the first therapy field within the tissue via the delivery of the therapy, by the implantable medical device, to the tissue of the patient according to the therapy program, wherein the change in the first therapy field occurs without change to the therapy program,
in response to reception of the information indicative of the change in the first therapy field, generate a first therapy field model based on the therapy program that is used to generate the first therapy field prior to the change in the first therapy field and the information indicative of the change in the first therapy field,
compare the first therapy field model to an algorithmic model of a baseline therapy field, and
modify the therapy program based on the comparison of the first therapy field model to the algorithmic model of the baseline therapy field.

17. The system of claim 16, further comprising a medical device programmer configured to communicate with the implantable medical device, wherein the medical device programmer comprises the processor.

18. The system of claim 16, further comprising a memory configured to store at least one of the algorithmic model of the baseline therapy field, hardware characteristics of the implantable medical device, hardware characteristics of a therapy delivery element coupled to the implantable medical device or patient anatomy data.

19. The system of claim 16, wherein the baseline therapy field comprises a known therapy field that results from delivery of stimulation according to at least one therapy program determined to deliver efficacious therapy.

20. The system of claim 16, further comprising a therapy system, wherein the therapy system comprises the implantable medical device, and wherein the information indicative of the change in the first therapy field comprises information indicative of a change in a hardware characteristic of the therapy system.

21. The system of claim 20, wherein the change in the hardware characteristic of the therapy system comprises at least one of a change in impedance of at least one electrode of a plurality of electrodes of the therapy system or an electrical path of the therapy system including the at least one electrode, an open circuit condition of at least one electrode of the plurality of electrodes, a change in location or orientation of at least one electrode of the plurality of electrodes, or a change in a hardware characteristic of the implantable medical device.

22. The system of claim 16, wherein the processor is configured to compare the first therapy field model to the algorithmic model of the baseline therapy field by at least comparing at least one field characteristic of the first therapy field model and the algorithmic model of the baseline therapy field.

23. The system of claim 22, wherein the field characteristic comprises at least one of stimulation volume, a centroid of stimulation, activated neurons, an amplitude of the voltage or current at a spatial point within the stimulation volume or a charge density.

24. The system of claim 16, wherein the processor is configured to modify the therapy program by at least modifying the therapy program to substantially maintain at least one field characteristic of the baseline therapy field.

25. The system of claim 16, wherein the implantable medical device comprises the processor.

26. A system comprising:
means for receiving information indicative of a change in a first therapy field, wherein the first therapy field was generated by prior delivery of therapy to a patient according to a therapy program, wherein prior to the change in the first therapy field, when therapy is delivered according to the therapy program, the first therapy field is generated, and wherein the change in the first therapy field occurs without change to the therapy program;
in response to receiving the information indicative of the change in the first therapy field, means for generating a first therapy field model based on the therapy program that is used to generate the first therapy field prior to the change in the first therapy field and the information indicative of the change in the first therapy field;
means for comparing the first therapy field model to an algorithmic model of a baseline therapy field; and
means for modifying the therapy program based on the comparison of the first therapy field model to the algorithmic model of the baseline therapy field.

27. The system of claim 26, wherein the baseline therapy field comprises a known therapy field that results from delivery of stimulation according to at least one therapy program determined to deliver efficacious therapy.

* * * * *